(12) United States Patent
Failli et al.

(10) Patent No.: US 7,687,623 B2
(45) Date of Patent: Mar. 30, 2010

(54) PYRROLOBENZODIAZEPINES AND HETEROCYCLIC CARBOXAMIDE DERIVATIVES AS FOLLICLE STIMULATING HORMONE RECEPTOR (FSH-R) ANTAGONISTS

(75) Inventors: Amedeo A. Failli, Princeton Junction, NJ (US); Dominick A. Quagliato, Bridgewater, NJ (US); Gavin Heffernan, Florence, NJ (US); Richard D. Coghlan, Phoenixville, PA (US); Emily S. Shen, West Chester, PA (US)

(73) Assignee: Wyeth LLC, Madison, NJ (US)

( * ) Notice: Subject to any disclaimer, the term of this patent is extended or adjusted under 35 U.S.C. 154(b) by 717 days.

(21) Appl. No.: 11/432,200

(22) Filed: May 11, 2006

(65) Prior Publication Data

US 2006/0258645 A1   Nov. 16, 2006

Related U.S. Application Data

(60) Provisional application No. 60/680,235, filed on May 12, 2005.

(51) Int. Cl.
*A61P 15/18* (2006.01)
*A61K 31/55* (2006.01)
*C07D 487/12* (2006.01)

(52) U.S. Cl. .................................................. 540/561
(58) Field of Classification Search .................. 540/561
See application file for complete search history.

(56) References Cited

U.S. PATENT DOCUMENTS

| | | | |
|---|---|---|---|
| 6,200,963 B1 | 3/2001 | Wrobel et al. | |
| 6,355,633 B1 | 3/2002 | Wrobel et al. | |
| 6,426,357 B1 | 7/2002 | Scheuerman et al. | |

FOREIGN PATENT DOCUMENTS

| | | |
|---|---|---|
| WO | WO 00/58277 A | 10/2000 |
| WO | WO 01/47875 | 7/2001 |
| WO | WO 00/08015 | 2/2002 |
| WO | WO 02/09705 | 2/2002 |
| WO | WO 02/09706 | 2/2002 |
| WO | WO 02/070493 | 9/2002 |
| WO | WO 02/083678 A | 10/2002 |
| WO | WO 02/083680 | 10/2002 |
| WO | WO 02/083683 | 10/2002 |
| WO | WO 02/083684 | 10/2002 |
| WO | WO 02/085907 A | 10/2002 |
| WO | WO 03/004028 | 1/2003 |
| WO | WO 2004/056779 A | 7/2004 |
| WO | WO 2004/056780 A2 | 7/2004 |

OTHER PUBLICATIONS

K. Aittomaki et al., "Mutations in the Follicle-Stimulating Hormone Receptor Gene Causes Hereditary Hypergonadotropic Ovarian Failure", Cell, 82: 959-968, (1995).
B.J. Arey et al., "Identification and Characterization of Selective, Non-peptide Follicle-Stimulating Hormone Receptor Antagonist", CL-272219, The Endrocine Society 82$^{nd}$ Annual Meeting, Toronto, Canada Jun. 21-24, 2000 and Endocrinology 143 (10), 3822 (2002).
Badone et al., "Highly Efficient Palladium-Catalyzed Boronic Acid Coupling Reactions in Water: Scope and Limitations", J. Org. Chem., 62: 7170-7173(1997).
Coffen et al., "2-Benzazepines. 8. Zerovalent nickel mediated biaryl synthesis of an anxiolytic pyrimido[5,4-d][2]benzazepine," *J Org Chem* 49(2):296-300(1984).
R. Danesi et al., "Clinical and Experimental Evidence of Inhibition of Testosterone Production by Suramin", J. Clin. Endocrinal. Metab., 81: 2238-2246 1996.
R.L. Daugherty et al., "Suramin Inhibits Gonadotropin Action in Rat Tests Implications for Treatment of Advanced Prostate Cancer", J. Urol, 147: 727 (1992).
Farina et al., "On the Nature of the "Copper Effect" in the Stille Cross-Coupling," *J Org Chem* (1994) 59(20):5905.
George, S.E. et al., "Evaluation of a CRE-directed luciferase reporter gene assay as an alternative to measuring cAMP accumulation", J. Biomol. Screening 2:235-240 1997.
Giroux et al., "One pot biaryl synthesis via in situ boronate formation," *Tetrahedron Lett* (1997) 38(22):3841-3844.
T. Guo et al., "Small molecule biaryl FSH receptor agonists. Part 1: Lead discovery via encoded combinatorial synthesis. Part 2 : Lead Optimization via Parallel synthesis", Bioorg. Med. Chem. Lett., 14: 1713-1720 (2004).
A.J. Hsueh et al., "Cells as Hormone Targets: The Role of Biologically Active Follicle-Stimulating Hormone in Reproduction", Rec. Prog. Horm. Res., 45: 209-227,1989.

(Continued)

*Primary Examiner*—Brenda L Coleman
(74) *Attorney, Agent, or Firm*—Pepper Hamilton LLP

(57) ABSTRACT

The invention provides compounds of formula

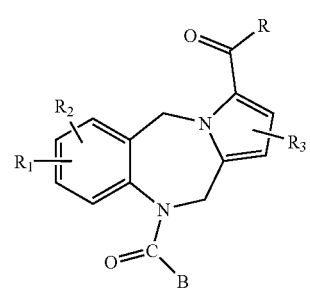

I or a pharmaceutically acceptable salt thereof, wherein R, $R_1$, $R_2$, $R_3$, and B are as defined in the accompanying specification. Methods of making such compounds are also provided.

51 Claims, No Drawings

OTHER PUBLICATIONS

Inanaga et al., "A Rapid Esterification by Means of Mixed Anhydride and Its Application to Large-ring Lactonization," *Bull Chem Soc Jpn* (1979) 52(7):1989-1993.

Ishiyama et al., "Palladium(0)-Catalyzed Cross-Coupling Reaction of Alkoxydiboron with Haloarenes: A Direct Procedure for Arylboronic Esters," *J Org Chem* (1995) 60(23):7508-7510.

Ishiyama et al., "Synthesis of arylboronates via the palladium(0)-catalyzed cross-coupling reaction of tetra(alkoxo)diborons with aryl triflates," *Tetrahedron Lett* (1997) 38(19):3447-3450.

Kelton, C.A. et al., , "The cloning of the human follicle stimulating hormone receptor and its expression in COS-7, CHO, and Y-1 cells", Mol. Cell. Endocrinol., 89:141-151 1992.

Lindstedt et al., "Follitropin (FSH) deficiency in an infertile male due to FSHbeta gene mutation. A syndrome of normal puberty and virilization but underdeveloped testicles with azoospermia, low FSH but high lutropin and normal serum testosterone concentrations," *Clin Chem Lab Med* (1998) 36(8):663-665.

March, *Advanced Organic Chemistry*, 3$^{rd}$ Edn., p. 647-648, John Wiley & Sons, New York (1985).

March, *Advanced Organic Chemistry*, 3$^{rd}$ Edn., p. 788 John Wiley & Sons, New York, (1985).

Mukherjee et al., "Gonadotropins induce rapid phosphorylation of the 3',5'-cyclic adenosine monophosphate response element binding protein in ovarian granulosa cells", Endocrinology, 137: 3234 (1996).

Quattropani et al., "Discovery and development of a new class of potent, selective, orally active oxytocin receptor antagonists," *J Med Chem* (2005) 48(24):7882-7905.

Schoenberg, et al., "Palladium-catalyzed amidation of aryl, heterocyclic, and vinylic halides," *J. Org. Chem.* (1974) 39(23):3327-3331.

Serradeil-Le Gal et al., "SSR126768A (4-chloro-3-[(3R)-(+)-5-chloro-1-(2,4-dimethoxybenzyl)-3- methyl-2-oxo-2,3-dihydro-1H-indol-3-yl]-N-ethyl-N-(3-pyridylmethyl)-benzamide, hydrochloride): a new selective and orally active oxytocin receptor antagonist for the prevention of preterm labor," *J Pharmacol Exper Ther* (2004) 309(1):414-424.

Shen "Palladium catalyzed coupling of aryl chlorides with arylboronic acids," *Tetrahedron Letters* (1997) 38(32):5575.

Street et al., "Synthesis and serotonergic activity of 5-(oxadiazolyl)tryptamines: potent agonists for 5-HT1D receptors", J. Med. Chem., 36: 1529 (1993).

Suzuki "New synthetic transformations via organoboron compounds," *Pure & Appl Chem* (1994) 66(2):213-222.

Tilly, J.L. et al., "Expression of recombinant human follicle-stimulating hormone receptor: Species-specific ligand binding, signal transduction, and identification of multiple ovarian messenger ribonucleic acid transcripts", Endocrinology, 131:799-806 1992.

Wolfe et al., "Highly Active Palladium Catalysts for Suzuki Coupling Reactions," *J Am Chem Soc* (1999) 121(41):9550-9561.

J. Wrobel et al., "Synthesis of (bis)Sulfonic Acid, (bis)Benzamides as Follicle-Stimulating Hormone (FSH) Antagonists", Bioorg. Med. Chem. 10: 639-656 (2002).

Wyatt et al., "Structure-activity relationship investigations of a potent and selective benzodiazepine oxytocin antagonist," *Bioorg Med Chem Letters* (2001) 11(10):1301-1305.

Wyatt et al., "Identification of potent and selective oxytocin antagonists. Part 1: indole and benzofuran derivatives," *Bioorg Med Chem Letters* (2002) 12(10)1399-1404.

Wyatt et al., "Identification of potent and selective oxytocin antagonists. Part 2: further investigation of benzofuran derivatives," *Bioorg Med Chem Letters* (2002) 12(10):1405-1411.

PYRROLOBENZODIAZEPINES AND HETEROCYCLIC CARBOXAMIDE DERIVATIVES AS FOLLICLE STIMULATING HORMONE RECEPTOR (FSH-R) ANTAGONISTS

This application claims benefit of priority to U.S. Provisional Patent Application No. 60/680,235 filed May 12, 2005, which is hereby incorporated in its entirety.

FIELD OF THE INVENTION

The present invention relates to pyrrolobenzodiazepines and derivatives thereof having antagonist activity on the FSH receptor, and to their use as contraceptives.

BACKGROUND OF THE INVENTION

Reproduction in women depends upon the dynamic interaction of several compartments of the female reproductive system. The hypothalamic-pituitary-gonadal axis orchestrates a series of events affecting the ovaries and the uterine-endometrial compartment that leads to the production of mature ova, ovulation, and ultimately appropriate conditions necessary for fertilization. Specifically, luteinizing hormone-releasing hormone (LHRH), released from the hypothalamus, initiates the release of the gonadotropins, luteneizing hormone (LH) and follicle stimulating hormone (FSH) from the pituitary. These hormones act directly on the ovary to promote the development of selected follicles by inducing granulosa and theca cell proliferation and differentiation. FSH stimulates aromatization of androgens to estrogens and increases the expression of LH receptors in the theca cells. The follicles, in turn, secrete steroids (estradiol, progesterone) and peptides (inhibin, activin). Estradiol and inhibin levels progressively increase during the follicular phase of the menstrual cycle until ovulation. Inhibin decreases FSH secretion from the pituitary gland, while estradiol acts on the hypothalamus and pituitary to induce the LH surge in mid-cycle, which results in ovulation. Afterwards, the post-ovulation, ruptured follicle forms the corpus luteum, which produces progesterone. Ovarian hormones, in turn, regulate the secretion of gonadotropins through a classical long-loop negative feedback mechanism. The elucidation of these control mechanisms has provided opportunities for the development of effective strategies to control fertility, including both enhancement of fertility and contraception. For recent reviews of FSH action see: "FSH Action and Intraovarian Regulation", B. C. J. M. Fauser Editor, Parthenon Publishing Group, Vol. 6, 1997 and A. J. Hsueh, T. Bicsak, X.-C. Ja, K. D. Dahl, B. C. J. M. Fauser, A. B. Galway, N. Czwkala, S. Pavlou, H. Pakoff, J. Keene, I. Boime, Granulosa "Cells as Hormone Targets: The Role of Biologically Active Follicle-Stimulating Hormone in Reproduction", Rec. Prog. Horm. Res., 45, 209-227, 1989.

Current hormonal contraception methods are steroidal in nature (progestins and estrogens) and modulate long-loop feedback inhibition of gonadotropin secretion, as well as affecting peripheral mechanisms such as sperm migration and fertilization. The development of specific antagonists of the receptor for FSH (FSH-R) would provide an alternative strategy for hormonal contraception. Such antagonists would block FSH-mediated follicular development leading to a blockade of ovulation, thereby producing the desired contraceptive effect. Support for the effectiveness of this strategy is provided by the mechanism that causes resistant ovary syndrome which results in infertility in women. The infertility experienced by these women is the result of non-functional FSH receptors (K. Aittomaki, J. L. D. Lucena, P. Pakarinen, P. Sistonen, J. Tapainainnen, J. Gromoll, R. Kashikari, E.-M. Sankila, H. Lehvaslaiho, A. R. Engel, E. Nieschlag, I. Huhtaniemi, A. de la Chapelle "Mutations in the Follicle-Stimulating Hormone Receptor Gene Causes Hereditary Hypergonadotropic Ovarian Failure" Cell, 82, 959-968, 1995). This approach to contraception may be applicable to men as well, since idiopathic male infertility seems to be related to a reduction in FSH binding sites. In addition, men with selective FSH deficiency are oligo- or azoospermic with normal testosterone levels and present normal virilization (G. Lindstedt, E. Nystrom, C. Matthews, I. Ernest, P. O. Janson, K. Chattarjee, Clin. Lab. Med., 36, 664, 1998). Therefore, orally active, low molecular weight FSH antagonists may provide a versatile novel method of contraception. Such an antagonist could be expected to interfere with follicle development and thus ovulation, while maintaining sufficient estrogen production and beneficial effects on bone mass.

FSH actions are mediated by binding of the hormone to a specific transmembrane G protein-coupled receptor exclusively expressed in the ovary, leading to activation of the adenyl cyclase system and elevation of intracellular levels of the second messenger cAMP (A. Mukherjee, O. K. Park-Sarge, K. Mayo, Endocrinology, 137, 3234 (1996)).

SUMMARY OF THE INVENTION

Some embodiments of the invention include a compound of formula I:

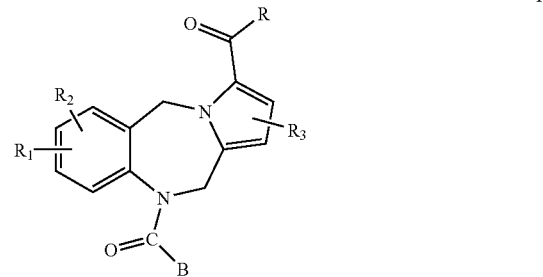

or a pharmaceutically acceptable salt thereof, wherein $R_1$ and $R_2$ are independently selected from hydrogen, ($C_1$-$C_6$)alkyl, halogen, cyano, trifluoromethyl, hydroxyl, ($C_1$-$C_6$) alkoxy, —$OCF_3$, carboxy, ($C_1$-$C_6$ alkoxy)carbonyl, —$CONH_2$, —CONH[($C_1$-$C_6$)alkyl], —CON[($C_1$-$C_6$) alkyl]$_2$, amino, ($C_1$-$C_6$)alkylamino or —NHCO[($C_1$-$C_6$) alkyl];

$R_3$ is a substituent selected from hydrogen, ($C_1$-$C_6$)alkyl, ($C_1$-$C_6$)alkoxy, hydroxy, amino, ($C_1$-$C_6$)alkylamino, —C(O) ($C_1$-$C_6$)alkyl, or halogen;

B is

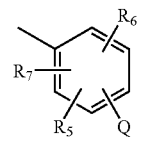

where Q is (a)
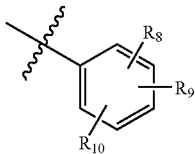

(b)
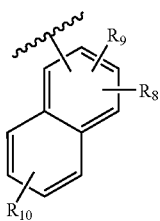

wherein $R_5$, $R_6$, $R_7$, $R_8$, $R_9$ and $R_{10}$ are independently, selected from the group consisting of hydrogen, alkyl, $(C_1-C_6)$alkyl, alkoxy, $(C_1-C_6)$alkoxy, hydroxyalkyl, hydroxy$(C_1-C_6)$alkyl, alkyloxyalkyl, $(C_1-C_6)$alkoxy $(C_1-C_6)$alkyl, $(C_2-C_7)$acyloxy$(C_1-C_6)$alkyl, $(C_1-C_6$alkyl)carbonyl, $(C_2-C_6)$alkenyl, $(C_2-C_6)$alkynyl, $(C_3-C_8)$cycloalkyl, formyl, $(C_3-C_8)$cycloalkylcarbonyl, carboxy, $(C_1-C_6)$alkoxycarbonyl, $(C_3-C_8$cycloalkyl)oxycarbonyl, aryl$(C_1-C_6)$alkyloxycarbonyl, carbamoyl, —O—CH$_2$—CH=CH$_2$, $(C_1-C_6)$alkyl substituted with 1-3 halogen atoms, trihalomethyl, trifluoromethyl, halogen, OCF$_3$, thioalkyl, thio$(C_1-C_6)$alkyl, —C(O)alkyl, —C(O)aryl optionally substituted by alkyl; hydroxy, —CH(OH)alkyl, —CH(alkoxy)alkyl, nitro, —SO$_2$alkyl, $(C_1-C_6)$alkylsulfonyl, aminosulfonyl, $(C_1-C_6)$alkylaminosulfonyl, —SO$_2$NHR$_{11}$, —SO$_2$N(R$_{11}$)$_2$, —OC(O)N[$(C_1-C_6)$alkyl]$_2$, —CONH[$(C_1-C_6)$alkyl], —CON[$(C_1-C_6)$alkyl]$_2$, —(CH$_2$)$_p$CN, $(C_1-C_6)$alkylamino, di-$(C_1-C_6)$alkylamino, $(C_1-C_6)$alkyl di-$(C_1-C_6)$alkylamino, —(CH$_2$)$_p$NR$_{13}$R$_{14}$, —(CH$_2$)$_p$CONR$_{13}$R$_{14}$, —(CH$_2$)$_p$COOR$_{12}$, —CH=NOH, —CH=NO—$(C_1-C_6)$alkyl, trifluoromethylthio,

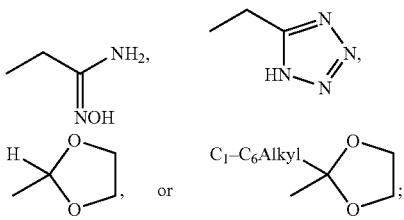

$R_{11}$ and $R_{12}$ are each independently hydrogen, $C_3-C_8$ cycloalkyl, or $(C_1-C_6)$alkyl;

$R_{13}$ and $R_{14}$ are each independently hydrogen, $C_3-C_8$ cycloalkyl, or $(C_1-C_6)$alkyl, or $R_{13}$ and $R_{14}$ can be taken together with the nitrogen to which they are attached to form a 4-6 membered saturated ring optionally containing O, S or N;

p is 0 or 1;

R is the moiety

$R_{15}$ is hydrogen or $(C_1-C_6)$alkyl;

Z has the formula —L—M;

L has the formula

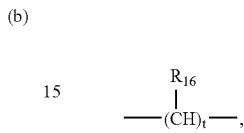

wherein t is an integer from 1 to 2;

$R_{16}$ is selected from the group consisting of hydrogen or $(C_1-C_6)$alkyl,

M is selected from the group consisting of

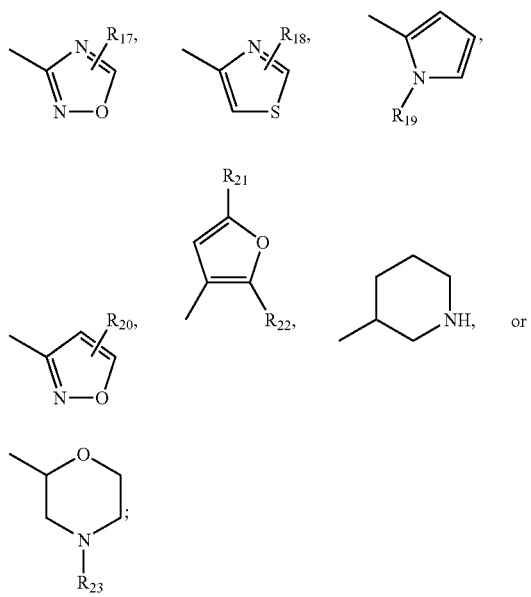

wherein $R_{17}$ and $R_{18}$ are optionally substituted aryl;

$R_{19}$, $R_{20}$, $R_{21}$, and $R_{22}$ are each independently $(C_1-C_6)$ alkyl;

$R_{23}$ is alkyl, $C_1-C_6$ alkyl, or an optionally substituted $(C_6-C_{20})$aralkyl.

Other embodiments of the invention provide methods of making such compounds or pharmaceutically acceptable salts thereof.

Other embodiments of the inventions will be apparent to those of skill in the art upon reading of the rest of this specification and claims.

DETAILED DESCRIPTION OF THE INVENTION

In some embodiments, the invention provides compounds of formula (I):

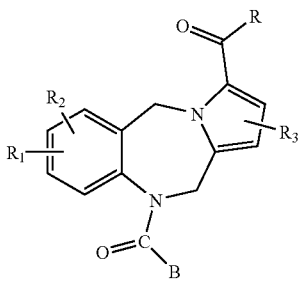

or a pharmaceutically acceptable salt thereof, wherein $R_1$ and $R_2$ are independently selected from hydrogen, $(C_1$-$C_6)$alkyl, halogen, cyano, trifluoromethyl, hydroxyl, $(C_1$-$C_6)$alkoxy, —$OCF_3$, carboxy, $(C_1$-$C_6$ alkoxy)carbonyl, —$CONH_2$, —$CONH[(C_1$-$C_6)$alkyl], —$CON[(C_1$-$C_6)$alkyl]$_2$, amino, $(C_1$-$C_6)$alkylamino or —$NHCO[(C_1$-$C_6)$alkyl];

$R_3$ is a substituent selected from hydrogen, $(C_1$-$C_6)$alkyl, $(C_1$-$C_6)$alkoxy, hydroxy, amino, $(C_1$-$C_6)$alkylamino, —$C(O)(C_1$-$C_6)$alkyl, or halogen;

B is

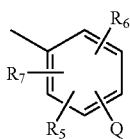

where Q is (a) 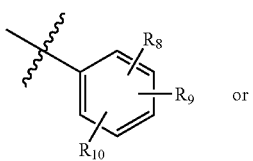

or (b) 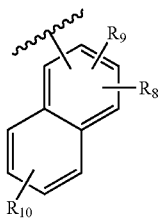

wherein $R_5$, $R_6$, $R_7$, $R_8$, $R_9$ and $R_{10}$ are independently, selected from the group consisting of hydrogen, alkyl, $(C_1$-$C_6)$alkyl, alkoxy, $(C_1$-$C_6)$alkoxy, hydroxyalkyl, hydroxy$(C_1$-$C_6)$alkyl, alkyloxyalkyl, $(C_1$-$C_6)$alkoxy$(C_1$-$C_6)$alkyl, $(C_2$-$C_7)$acyloxy$(C_1$-$C_6)$alkyl, $(C_1$-$C_6$alkyl)carbonyl, $(C_2$-$C_6)$alkenyl, $(C_2$-$C_6)$alkynyl, $(C_3$-$C_8)$cycloalkyl, formyl, $(C_3$-$C_8)$cycloalkylcarbonyl, carboxy, $(C_1$-$C_6)$alkoxycarbonyl, $(C_3$-$C_8$cycloalkyl)oxycarbonyl, aryl$(C_1$-$C_6)$alkyloxycarbonyl, carbamoyl, —O—$CH_2$—$CH$=$CH_2$, $(C_1$-$C_6)$alkyl substituted with 1-3 halogen atoms, trihalomethyl, trifluoromethyl, halogen, $OCF_3$, thioalkyl, thio$(C_1$-$C_6)$alkyl, —C(O)alkyl, —C(O)aryl optionally substituted by alkyl; hydroxy, —CH(OH)alkyl, —CH(alkoxy)alkyl, nitro, —$SO_2$alkyl, $(C_1$-$C_6)$alkylsulfonyl, aminosulfonyl, $(C_1$-$C_6)$alkylaminosulfonyl, —$SO_2NHR_{11}$, —$SO_2N(R_{11})_2$, —$OC(O)N[(C_1$-$C_6)$alkyl]$_2$, —$CONH[(C_1$-$C_6)$alkyl], —$CON[(C_1$-$C_6)$alkyl]$_2$, —$(CH_2)_pCN$, $(C_1$-$C_6)$alkylamino, di-$(C_1$-$C_6)$alkylamino, $(C_1$-$C_6)$alkyl di-$(C_1$-$C_6)$alkylamino, —$(CH_2)_pNR_{13}R_{14}$, —$(CH_2)_pCONR_{13}R_{14}$, —$(CH_2)_pCOOR_{12}$, —CH=NOH, —CH=NO—$(C_1$-$C_6)$alkyl, trifluoromethylthio,

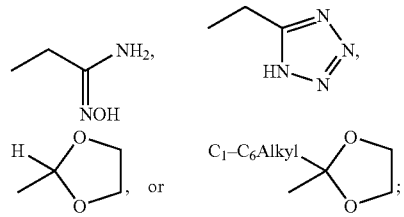

$R_{11}$ and $R_{12}$ are each independently hydrogen, $C_3$-$C_8$ cycloalkyl, or $(C_1$-$C_6)$alkyl;

$R_{13}$ and $R_{14}$ are each independently hydrogen, $C_3$-$C_8$ cycloalkyl, or $(C_1$-$C_6)$alkyl, or $R_{13}$ and $R_{14}$ can be taken together with the nitrogen to which they are attached to form a 4-6 membered saturated ring optionally containing O, S or N;

p is 0 or 1;

R is the moiety

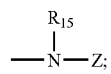

$R_{15}$ is hydrogen or $(C_1$-$C_6)$alkyl;

Z has the formula —L—M;

L has the formula

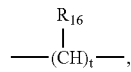

wherein t is an integer from 1 to 2;

$R_{16}$ is selected from the group consisting of hydrogen or $(C_1$-$C_6)$alkyl, M is selected from the group consisting of

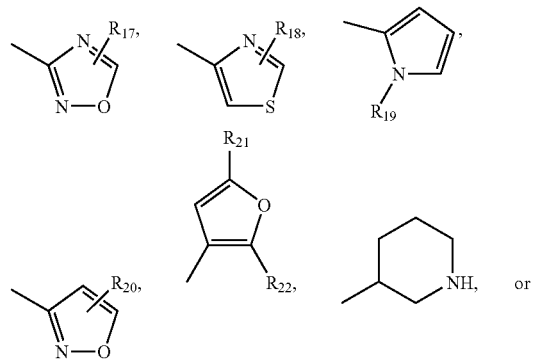

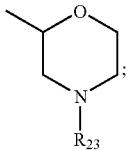

wherein $R_{17}$ and $R_{18}$ are optionally substituted aryl; $R_{19}, R_{20}, R_{21}$ and $R_{22}$ are each independently ($C_1$-$C_6$) alkyl;

$R_{23}$ is alkyl, $C_1$-$C_6$ alkyl, or an optionally substituted ($C_6$-$C_{20}$)aralkyl.

Acyl, as used herein, refers to the group R—C(═O)— where R is an alkyl group of 1 to 6 carbon atoms. For example, a $C_2$ to $C_7$ acyl group refers to the group R—C(═O)— where R is an alkyl group of 1 to 6 carbon atoms. One suitable acyl is acetyl.

Alkenyl, as used herein, refers to an alkyl group having one or more double carbon-carbon bonds. Example alkenyl groups include, but are not limited to, ethenyl, propenyl, butenyl, pentenyl, hexenyl, butadienyl, pentadienyl, and hexadienyl. In some embodiments, alkenyl groups can be substituted with up to four substituent groups, as described below. Suitably the alkenyl is a 2 to 6 carbon moiety.

Alkoxy, as used herein, refers to an —O-alkyl group. Example alkoxy groups include methoxy, ethoxy, propoxy (e.g., n-propoxy and isopropoxy), t-butoxy, and the like. An alkoxy group can contain from 1 to about 20, 1 to about 10, 1 to about 8, 1 to about 6, 1 to about 4, or 1 to about 3 carbon atoms. In some embodiments, alkoxy groups can be substituted with up to four substituent groups, as described below.

Alkoxyalkyl, employed alone or in combination with other terms, refers to an alkoxy, as herein before defined, which is further covalently bonded to an unsubstituted ($C_1$-$C_{10}$) straight chain or unsubstituted ($C_2$-$C_{10}$) branched-chain hydrocarbon. Examples of alkoxyalkyl moieties include, but are not limited to, chemical groups such as methoxymethyl, —$CH_2CH(CH_3)OCH_2CH_3$, and homologs, isomers, and the like. In certain embodiments the alkoxyalkyl moiety is a ($C_1$-$C_6$)alkoxy($C_1$-$C_6$)alkyl or a ($C_1$-$C_4$)alkoxy($C_1$-$C_4$)alkyl moiety.

Alkoxycarbonyl, employed alone or in combination with other terms, is defined herein as, unless otherwise stated, an alkoxy group, as herein before defined, which is further bonded to a carbonyl group to form an ester moiety. Examples of alkoxycarbonyl moieties include, but are not limited to, chemical groups such as methoxycarbonyl, ethoxycarbonyl, isopropoxycarbonyl, sec-butoxycarbonyl, tert-butoxycarbonyl, decanoxycarbonyl, and homologs, isomers, and the like.

Alkyl is meant to refer to a saturated hydrocarbon group which is straight-chained or branched. Example alkyl groups include, but are not limited to, methyl(Me), ethyl(Et), propyl (e.g., n-propyl and isopropyl), butyl (e.g., n-butyl, isobutyl, s-butyl, t-butyl), pentyl (e.g., n-pentyl, isopentyl, neopentyl) and the like. Alkyl groups can contain from 1 to about 20, 1 to about 10, 1 to about 8, 1 to about 6, 1 to about 4, or 1 to about 3 carbon atoms. In some embodiments, alkyl groups can be substituted with up to four substituent groups, as described below. Lower alkyl is intended to mean alkyl groups having up to six carbon atoms.

Alkylamino, employed alone or in combination with other terms, refers to a moiety with one alkyl group, wherein the alkyl group is an unsubstituted ($C_1$-$C_6$) straight chain herein before defined alkyl group or an unsubstituted ($C_3$-C8) herein before defined cycloalkyl group. Examples of alkylamino moieties include, but are not limited to, chemical groups such as —$NH(CH_3)$, —$NH(CH_2CH_3)$, —NH-cyclopentyl, and homologs, and the like.

Alkylaminosulfonyl employed alone, or unless otherwise stated, is an alkylamino moiety, as herein before defined, which is further bonded to a sulfonyl group.

Alkylsulfonyl, as used herein, refers to the group R—S(O)$_2$— where R is an alkyl group, as herein before defined.

Alkynyl, as used herein, refers to an alkyl group having one or more triple carbon-carbon bonds. Examples of alkynyl groups include, but are not limited to, ethynyl, propynyl, butynyl, pentynyl, and the like. In some embodiments, alkynyl groups can be substituted with up to four substituent groups, as described below. The alkynyl moiety is suitably a 2 to 6 carbon atom alkynyl.

Aroyl, as used herein, refers to the group Ar—C(═O)— where Ar is aryl as defined below. For example, a $C_6$ to $C_{14}$ aroyl moiety refers to the group Ar—C(═O)— where Ar is an aromatic 6 to 14 or 5 to 13 membered carbocylic ring.

Aryl, as used herein, refers to aromatic carbocyclic groups including monocyclic or polycyclic aromatic hydrocarbons such as, for example, phenyl, 1-naphthyl, 2-naphthyl, anthracenyl, phenanthrenyl, and the like. In some embodiments, aryl groups have from 5 to about 20 carbon atoms. In some preferred embodiments, aryl groups are phenyl or naphthyl groups that optionally contain up to four, preferably up to 2, substituent groups as described below. The aryl moiety is suitably a 6 to 14 carbon atom moiety.

Arylalkyl or aralkyl, as used herein, refers to a group of formula -alkyl-aryl, wherein aryl is as herein before defined. Preferably, the alkyl portion of the arylalkyl group is a lower alkyl group, i.e., a $C_1$-$C_6$ alkyl group, more preferably a $C_1$-$C_3$ alkyl group. Examples of aralkyl groups include, but are not limited to, benzyl and naphthylmethyl groups. In some preferred embodiments, arylalkyl groups can be optionally substituted with up to four, preferably up to 2, substituent groups.

Aryloxy, as used herein, refers to an —O-aryl group, wherein aryl is as hereinbefore defined for example and not limitation, phenoxy.

Carbamoyl, as used herein, refers to the group, —C(═O)N<.

Carbonyl, employed alone or in combination with other terms, is defined herein as, unless otherwise stated, a bivalent one-carbon moiety further bonded to an oxygen atom with a double bond. An example is

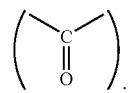

Carboxy as employed herein refers to —COOH.

Cyano, as used herein, refers to CN.

Cycloalkyl, as used herein, refers to non-aromatic carbocyclic groups including cyclized alkyl, alkenyl, and alkynyl groups. Cycloalkyl groups can be monocyclic (e.g., cyclohexyl) or poly-cyclic (e.g. 2, 3, or 4 fused ring) ring systems. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarenyl, adamantyl, and the like. Also included in the definition of cycloalkyl are moieties that have one or more aromatic rings fused (i.e., having a bond in common with) to the cycloalkyl ring, for example, benzo derivatives of cyclopentane(indanyl), cyclohexane(tetrahydronaphthyl), and the like.

Cycloalkylalkyl, as used herein, refers to a group of formula -alkyl-cycloalkyl, for example a cyclopropylmethyl group. The alkyl group is suitably a $C_1$ to $C_6$ alkyl as defined above and the cycloalkyl group is as defined above.

Cycloalkylcarbonyl, as used herein, refers to a group of formula -carbonyl-cycloalkyl, for example cyclohexylcarbonyl. The cycloalkyl moiety is as defined above.

Dialkylamino, employed alone or in combination with other terms, or unless otherwise stated, is a moiety with two independent alkyl groups, wherein the alkyl groups are unsubstituted ($C_1$-$C_6$) straight chain herein before defined alkyl groups or unsubstituted ($C_3$-$C_8$) herein before defined cycloalkyl groups. The two groups may be linked together to form an unsubstituted ($C_1$-$C_6$)-alkylene- group. Examples of dialkylamino moieties include, but are not limited to, chemical groups such as —N(CH$_3$)$_2$, —N(CH$_2$CH$_3$)$_2$, —NCH$_3$(CH$_2$CH$_3$),

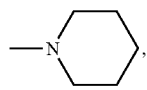

and homologs, and the like.

Dialkylaminoalkyl employed alone or in combination with other terms, or unless otherwise stated, is a dialkylamino moiety, as herein before defined, which is further covalently bonded to a straight chain alkyl group of 1-6 carbon atoms. Examples of dialkylaminoalkyl moieties include, but are not limited to, chemical groups such as —CH$_2$N(CH$_3$)$_2$, —CH$_2$CH$_2$N(CH$_2$CH$_3$)$_2$, —CH$_2$CH$_2$CH$_2$NCH$_3$(CH$_2$CH$_3$), and homologs, and the like.

Halo or halogen includes fluoro, chloro, bromo, and iodo.

Hünig's Base is N,N-diisopropylethylamine, also indicated herein as i-Pr$_2$NEt.

Hydroxy or hydroxyl, as used herein, refers to OH.

Hydroxyalkyl, employed alone or in combination with other terms, is defined herein as, unless otherwise stated, a ($C_1$-$C_{10}$) straight chain hydrocarbon, e.g. a ($C_1$-$C_6$) alkylterminally substituted with a hydroxyl group. Examples of hydroxyalkyl moieties include, but are not limited to, chemical groups such as —CH$_2$OH, —CH$_2$CH$_2$OH, —CH$_2$CH$_2$CH$_2$OH, and higher homologs.

Nitro, employed alone or in combination with other terms, is defined herein as, —NO$_2$.

Substituted, as used herein, refers to a moiety, such as an aryl or heteroaryl, having from 1 to about 5 substituents, and more preferably from 1 to about 3 substituents independently selected from a halogen atom, a cyano group, a nitro group, a hydroxyl group, a $C_1$-$C_6$ alkyl group, or a $C_1$-$C_6$ alkoxy group. Preferred substituents are a halogen atom, a hydroxyl group, or a $C_1$-$C_6$ alkyl group.

Thioalkyl, employed alone or in combination with other terms, is defined herein as sulfur covalently bonded to an alkyl group e.g. a ($C_1$-$C_6$)alkyl group as defined above.

At various places in the specification, substituents of compounds of the invention are disclosed in groups or in ranges. It is specifically intended that the invention include each and every individual subcombination of the members of such groups and ranges. For example, the term $C_{1-6}$ alkyl is specifically intended to individually disclose methyl, ethyl, propyl, isopropyl, n-butyl, sec-butyl, isobutyl, etc. Some embodiments provide such compounds wherein R$_{15}$ and R$_{16}$ are each hydrogen; and t is 1. Still further embodiments provide compounds wherein M is selected from the group consisting of

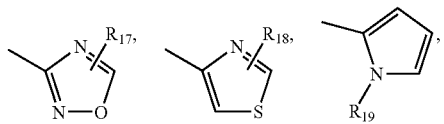

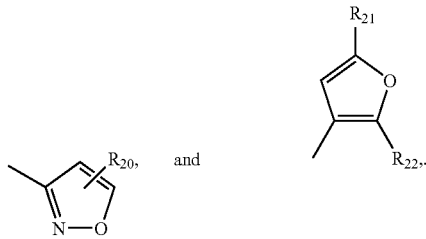

In other embodiments, the invention provides such compounds wherein M is selected from the group consisting of

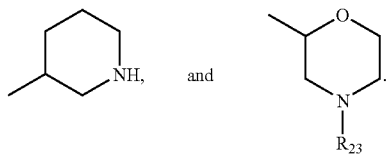

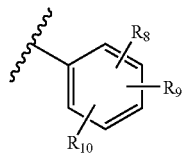

In some embodiments, Q is (a) and, thus, B has the formula:

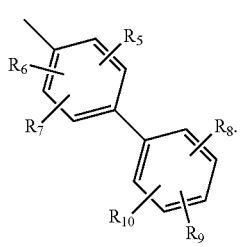

In some embodiments, the invention provides compounds wherein R$_1$, R$_2$ and R$_3$ are each hydrogen.

In some embodiments, the invention provides compounds of formula I having the Formula:

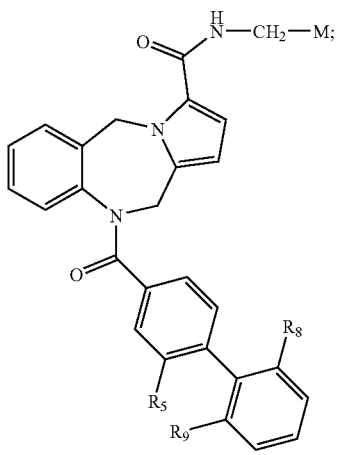

or a pharmaceutically acceptable salt thereof. In some such embodiments, $R_5$ is selected from H, or $C_1$-$C_3$ alkyl. In some further embodiments, $R_8$ and $R_9$ are independently selected from H, $C_1$-$C_3$ alkyl, or $C_1$-$C_3$ alkoxy.

In other such embodiments, $R_5$ is selected from H, or $C_1$-$C_3$ alkyl; and $R_8$ and $R_9$ are independently selected from H, $C_1$-$C_3$ alkyl, or $C_1$-$C_3$ alkoxy. In some further embodiments, M is

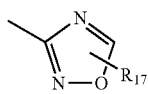

wherein $R_{17}$ is an optionally substituted aryl. In some embodiments, $R_{17}$ is phenyl, optionally substituted with from 1 to 3 substitutents selected from $C_1$-$C_3$ alkyl, $C_1$-$C_3$ alkoxy, and halogen. In some embodiments, $C_1$-$C_3$ alkoxy is methoxy.

In some embodiments, $R_5$ is selected from H, or $C_1$-$C_3$ alkyl; and $R_8$ and $R_9$ are independently selected from H, $C_1$-$C_3$ alkyl, or $C_1$-$C_3$ alkoxy and M is

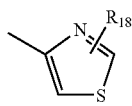

wherein $R_{18}$ is an optionally substituted aryl. In some such embodiments, $R_{18}$ is phenyl, optionally substituted with from 1 to 3 substitutents selected from $C_1$-$C_3$ alkyl, $C_1$-$C_3$ alkoxy, and halogen. In some embodiments, the halogen is chlorine.

In some embodiments, $R_5$ is selected from H, or $C_1$-$C_3$ alkyl; and $R_8$ and $R_9$ are independently selected from H, $C_1$-$C_3$ alkyl, or $C_1$-$C_3$ alkoxy and M is

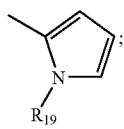

wherein $R_{19}$ is $C_1$-$C_6$ alkyl, preferably methyl.

In some embodiments, $R_5$ is selected from H, or $C_1$-$C_3$ alkyl; and $R_8$ and $R_9$ are independently selected from H, $C_1$-$C_3$ alkyl, $C_1$-$C_3$ alkoxy and M is

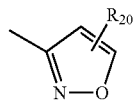

wherein $R_{20}$ is $C_1$-$C_6$ alkyl, preferably methyl.

In some embodiments, $R_5$ is selected from H, or $C_1$-$C_3$ alkyl; and $R_8$ and $R_9$ are independently selected from H, $C_1$-$C_3$ alkyl, or $C_1$-$C_3$ alkoxy and M is

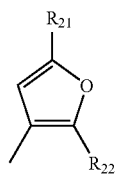

wherein $R_{21}$ and $R_{22}$ are each independently $C_1$-$C_6$ alkyl. In some embodiments, the invention provides such compounds where $R_{21}$ and $R_{22}$ are the same. In some embodiments, $R_{21}$ and $R_{22}$ are each methyl.

In some embodiments, $R_5$ is selected from H, or $C_1$-$C_3$ alkyl; and $R_8$ and $R_9$ are independently selected from H, $C_1$-$C_3$ alkyl, or $C_1$-$C_3$ alkoxy and M is

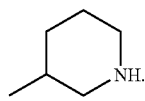

In some embodiments, $R_5$ is selected from H, and $C_1$-$C_3$ alkyl; and $R_8$ and $R_9$ are independently selected from H, $C_1$-$C_3$ alkyl, $C_1$-$C_3$ alkoxy and M is

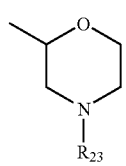

wherein $R_{23}$ is optionally substituted $C_6$-$C_{20}$ aralkyl, preferably benzyl.

In some embodiments, the invention provides compounds according to claim 1, wherein M is

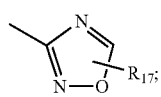

wherein $R_{17}$ is an optionally substituted aryl. In some embodiments, the invention further provides such compounds wherein $R_{17}$ is a phenyl, optionally substituted with from 1 to 3 substituents selected from $C_1$-$C_3$ alkyl, $C_1$-$C_3$ alkoxy, and halogen. In some embodiments, the $C_1$-$C_3$ alkoxy of said $R_{17}$ is methoxy.

In some such embodments, M is

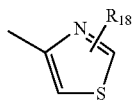

wherein $R_{18}$ is an optionally substituted aryl. In some such embodiments, $R_{18}$ is a phenyl, optionally substituted with from 1 to 3 substituents selected from $C_1$-$C_3$ alkyl, $C_1$-$C_3$ alkoxy, and halogen, preferably chlorine.

In other embodiments, the invention provides compounds of formula I, and pharmaceutically acceptable salts thereof, M is

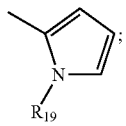

wherein $R_{19}$ is $C_1$-$C_6$ alkyl, preferably methyl.

In other embodiments, the invention provides compounds of formula I, and pharmaceutically acceptable salts thereof, wherein M is

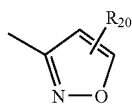

wherein $R_{20}$ is $C_1$-$C_6$ alkyl, preferably methyl.

In other embodiments, the invention provides compounds of formula I, and pharmaceutically acceptable salts thereof, M is

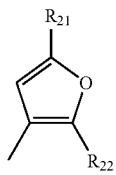

wherein $R_{21}$ and $R_{22}$ are each independently $C_1$-$C_6$ alkyl. In some embodiments, $R_{21}$ and $R_{22}$ are the same. In some such embodiments, $R_{21}$ and $R_{22}$ are each methyl.

In other embodiments, the invention provides compounds of formula I, and pharmaceutically acceptable salts thereof, wherein M is

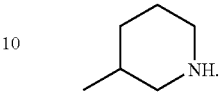

In other embodiments, the invention provides compounds of formula I, and pharmaceutically acceptable salts thereof, wherein M is

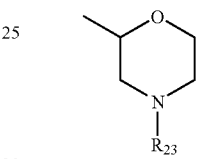

wherein $R_{23}$ is optionally substituted $C_7$-$C_{20}$ aralkyl, preferably benzyl.

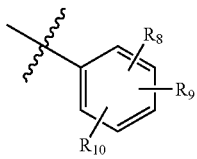

In some embodiments, Q is (a) and, thus, B has the formula:

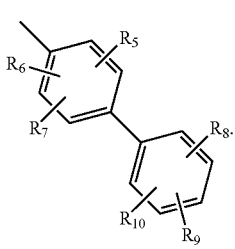

Other embodiments will be readily ascertainable to those of skill in the art upon reading this specification and claims.

Exemplary compounds according to Formula I include, but are not limited to, those in the following table:

| Example | Structure |
|---|---|
| 2 | 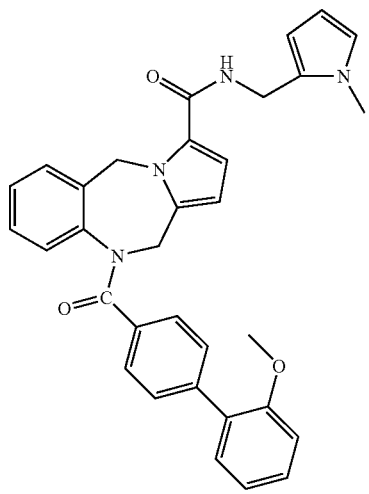 |
| 4 | 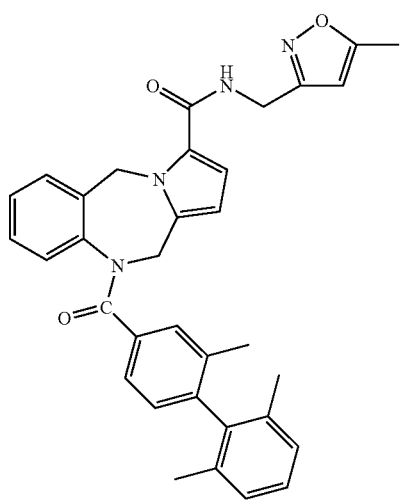 |
| 5 | 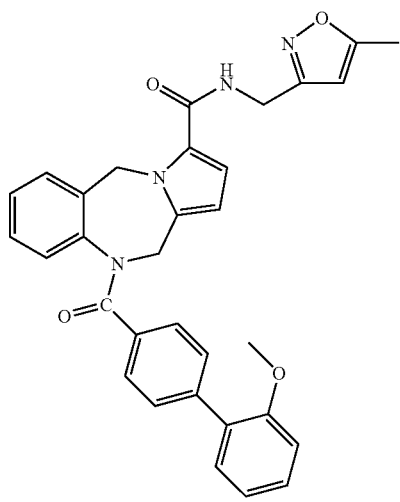 |

-continued
| Example | Structure |
|---|---|
| 6 | 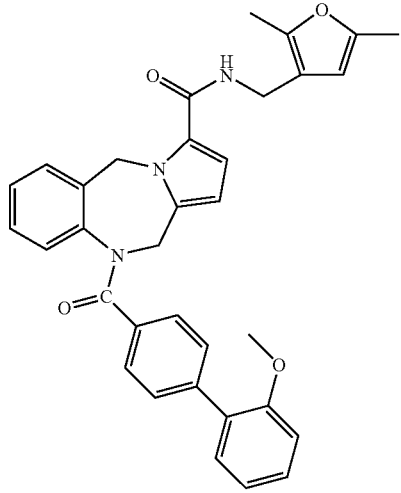 |
| 7 | 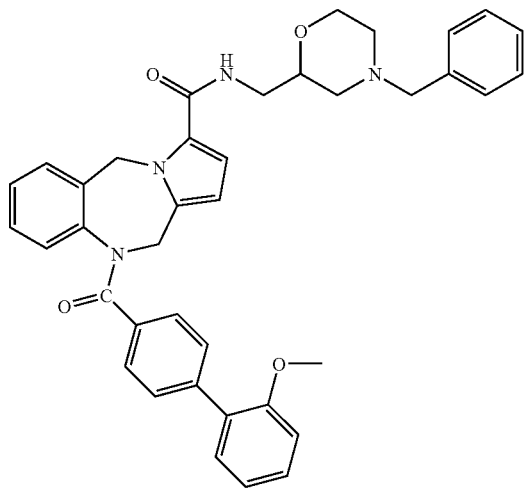 |
| 8 | 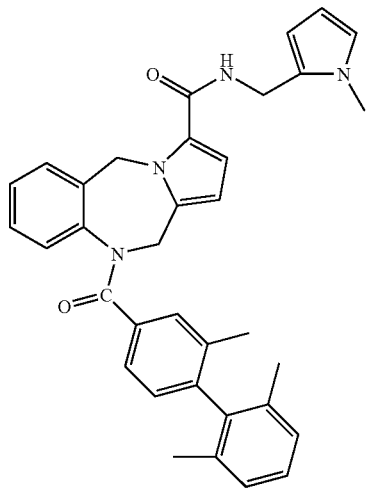 |

-continued
| Example | Structure |
|---------|-----------|
| 10 | 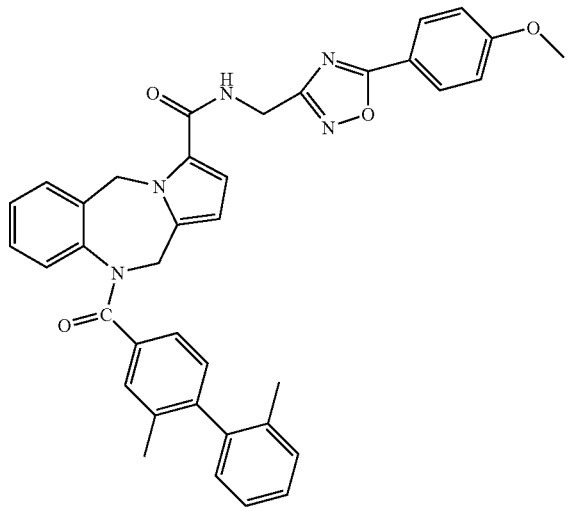 |
| 11 | 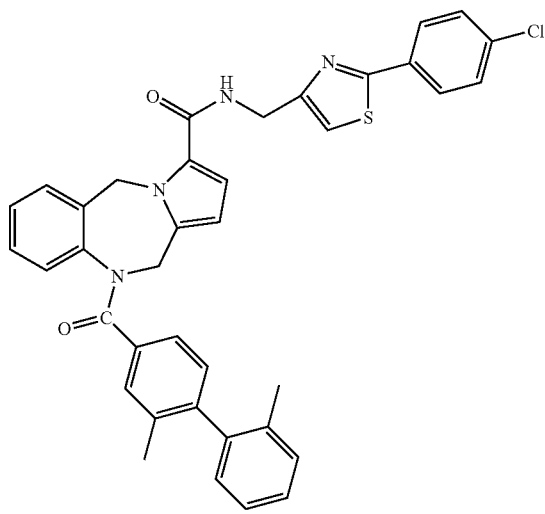 |
| 12 | 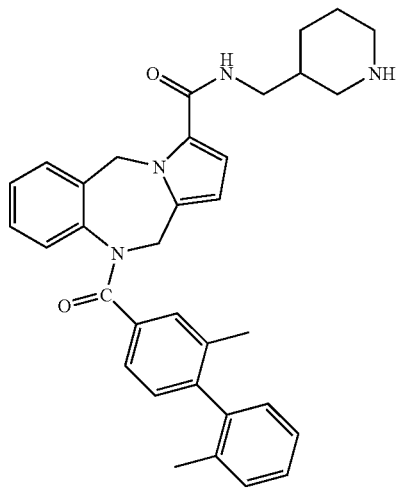 |

It is understood by those practicing the art that some of the compounds of this invention, depending on the definition of the various substituents, can contain one or more asymmetric centers, and can give rise to enantiomers and diastereomers. The present invention includes all stereoisomers including individual diastereomers and resolved, enantiomerically pure R and S stereoisomers; as well as racemates, and all other mixtures of R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, E-Z isomers, endo-exo isomers, and mixtures thereof which posses the indicated activity. Such isomers can be obtained in pure form by standard procedures known to those skilled in the art.

It is understood by those practicing the art that some of the compounds of this invention, depending on the definition of B, may be chiral due to hindered rotation, and give rise to atropisomers which can be resolved and obtained in pure form by standard procedures known to those skilled in the art. Also included in this invention are all polymorphs and hydrates of the compounds of the present invention.

The invention also includes pharmaceutically acceptable salts of the compounds of formula I. By "pharmaceutically acceptable salt", it is meant any compound formed by the addition of a pharmaceutically acceptable base and a compound of formula I to form the corresponding salt. By the term "pharmaceutically acceptable" it is meant a substance that is acceptable for use in pharmaceutical applications from a toxicological perspective and does not adversely interact with the active ingredient. Pharmaceutically acceptable salts, including mono- and bi-salts, include, but are not limited to, those derived from such organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Other embodiments of the invention provide methods for preparing a compound of formula I, or pharmaceutically acceptable salts thereof, described above wherein the method comprises reacting a trichloroacetyl compound of formula (2)

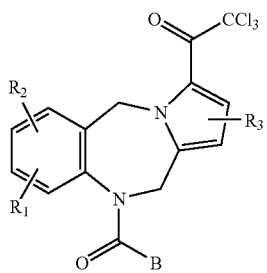

2 where, $R_1$, $R_2$, $R_3$, and B are defined above, with an appropriately substituted primary or secondary amine of formula (3)

RH (3)

where R is defined above, under conditions sufficient to yield a compound of Formula (I). In some embodiments, the reaction occurs in the presence of 1,4-dioxane, dimethylsulfoxide, or both. In some embodiments, the reaction occurs in the presence of an organic base. In some embodiments, the organic base is a tertiary amine, preferably triethyl amine or N,N-diisopropylethylamine. In some embodiments, the reaction is performed in a solvent, such as, but not limited to, acetonitrile. When solvent is present, the reaction is performed at a temperature of from about ambient to the refluxing temperature of the solvent.

In some embodiments, the trichloroacetyl compound of formula (2) is prepared by reacting a tricyclic azepine of formula (1)

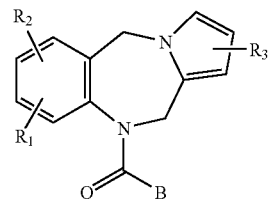

1 where, $R_1$, $R_2$, $R_3$, and B are defined above, with perhaloalkanoyl halide under conditions sufficient to provide the desired trichloroacetyl compound of formula (2). In some embodiments, the perhaloalkanoyl halide is trichloroacetyl chloride. In some embodiments, the reaction occurs in the presence of an organic base, such as, but not limited to, N,N-diisopropylethyl amine, in an aprotic organic solvent. The organic solvent may be any suitable aprotic organic solvent, such as but not limited to dichloromethane or 1,4-dioxane. In some such embodiments, the reaction is performed at temperatures of from about −10° C. to about ambient.

Some embodiments of the invention provide methods for making a compound of Formula I comprising coupling a compound of Formula (4)

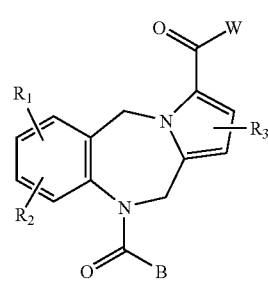

4 where, $R_1$, $R_2$, $R_3$, and B are defined above, where W is OH or halogen, with an appropriately substituted primary or secondary amine of formula (3)

RH (3)

where R is defined above, under conditions sufficient to yield a compound of formula (I) of claim 1. In some embodiments, W is Cl or Br. In some embodiments, the coupling of the acyl halide of formula (4) with the substituted amine of formula (3) is performed in the presence of a tertiary amine in an aprotic solvent. Suitable aprotic solvents include, but are not limited to, dichloromethane, N,N-dimethylformamide, and tetrahydrofuran. An exemplary tertiary amine is N,N-diisopropylethylamine. In some embodiments, the coupling of the acyl halide of formula (4) with the substituted amine of formula (3) is performed at a temperature of from about ambient to the reflux temperature of the solvent.

In other embodiments, W is OH.

Amidation

In some embodiments, the coupling comprises reacting the carboxylic acid (4) with a primary or secondary amine of formula (3) in the presence of at least one of an activating reagent or a coupling reagent under conditions sufficient to yield a compound of formula (I). Suitable activating agents include, but are not limited to, triphosgene in an aprotic solvent, N,N-dicyclohexylcarbodiimide, 1-ethyl-3-(3-dimethylamino-propyl)carbodiimide hydrochloride in the presence of 1-hydroxy benzotriazole; or N,N'-carbonyldiimidazole in an aprotic solvent. In some such embodiments, the reaction occurs in the presence of an organic base, such as but not limited to the tertiary amines. The organic base can be, but is not limited to, N,N-diisopropylethylamine.

In some embodiments, the reaction is performed in the presence of a catalyst, such as but not limited to, 4-(dimethylamino)pyridine.

In some embodiments, the coupling reagent is selected from hydroxybenzotriazole tetramethyluronium hexafluorophosphate, diphenylphosphoryl azide, diethyl cyano phosphonate, or benzotriazol-1-yl-oxy-tris-(dimethylamino) phosphonium hexafluorophosphate.

Acylation

Some embodiments of the invention provide methods for making a compound of Formula I comprising coupling a compound of Formula (4)

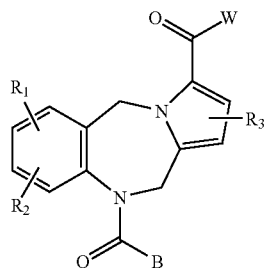

4 where, $R_1$, $R_2$, $R_3$, and B are defined above, wherein W is Cl or Br, which is prepared by conversion of a compound of Formula 4 wherein W is OH, with an appropriately substituted primary or secondary amine of formula (3)

RH    (3)

where R is defined above, under conditions sufficient to yield a compound of formula (I). In some such embodiments, the conversion process comprises reacting a compound of Formula 4 wherein W is OH with thionyl halide or an oxalyl halide. In some embodiments, conversion occurs in the presence of at least one of an inorganic base, such as but not limited to potassium carbonate, and an organic base in an aprotic solvent. In some embodiments, the organic base includes but is not limited to, pyridine, 4-(dimethylamino)pyridine, or a tertiary amine, such as but not limited to triethylamine. Suitable aprotic solvents include, but are not limited to, dichloromethane, N,N-dimethylformamide, and tetrahydrofuran. In some embodiments, conversion is performed at a temperature of from about −5° C. to about 50° C.

Some embodiments of the invention provide methods of preparing a compound of Formula I comprising reacting a tricyclic diazepine of formula (1)

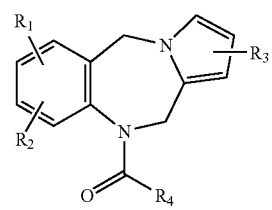

1 where, $R_1$, $R_2$, $R_3$, and B are defined above, with diphosgene and a primary or secondary amine of formula (3)

RH    (3)

where R is defined above, in an aprotic solvent under conditions sufficient to yield a compound according to formula (I). Any suitable aprotic solvent can be used, including but not limited to, dichloromethane. In some embodiments, the reaction occurs in the presence of an organic base, such as but not limited to triethylamine.

General Synthetic Scheme(s) for Preparation of Compounds

The compounds of the present invention can be prepared according to one or more of the general processes outlined below.

The compounds of general formula (I) wherein B is

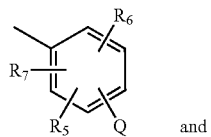

(a)

Q is 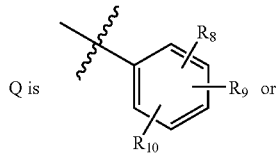 or (b)

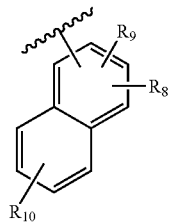

can be conveniently prepared as shown in Scheme I.

Scheme I

According to the above preferred process, a tricyclic azepine of formula (1) wherein $R_1$, $R_2$, $R_3$ and B are defined hereinbefore, is reacted with perhaloalkanoyl halide, preferably trichloroacetyl chloride, in the presence of an organic base such as, but not limited to, N,N-diisopropylethyl amine (Hünig's base) in an aprotic organic solvent such as, but not limited to, dichloromethane or 1,4-dioxane, at temperatures ranging from about −10° C. to about ambient, to provide the desired trichloroacetyl intermediate of formula (2). Subsequent reaction of the intermediate of formula (2) with an appropriately substituted primary or secondary amine of formula (3) in refluxing 1,4-dioxane or with dimethylsulfoxide optionally in the presence of an organic base such triethylamine, in a solvent such as, but not limited to, acetonitrile, at temperatures ranging from about ambient to the refluxing temperature of the solvent, yields the desired compounds of formula (I) wherein $R_1$, $R_2$, $R_3$ and B are as defined hereinbefore.

Another preferred process is shown in Scheme II below.

Scheme II

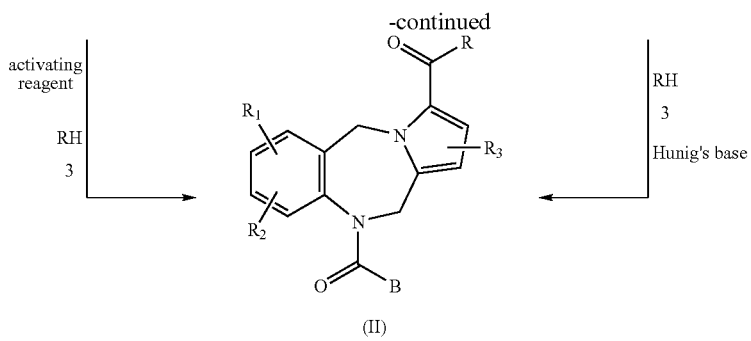

(II)

According to the above preferred process the trichloroacetyl intermediate of formula (2) is hydrolyzed with aqueous base such as, but not limited to, sodium hydroxide, in an organic solvent such as, but not limited to, tetrahydrofuran or acetone at temperatures ranging from about −10° C. to about ambient, to yield the intermediate acid of formula (4). The required activation of the carboxylic acid (4) for the subsequent coupling with a primary or secondary amine of formula (3) can be accomplished in several ways. Thus, the intermediate of formula (4) can be converted to an acyl halide preferably a chloride or bromide of formula (5), where J is COCl or COBr, by reaction with thionyl chloride, thionyl bromide, oxalyl chloride, or oxalyl bromide or similar reagents known in the art, either neat or in the presence of an inorganic base such as, but not limited to, potassium carbonate, or in the presence of an organic base such as, but not limited to, pyridine, 4-(dimethylamino)pyridine, or a tertiary amine such as, but not limited to, triethylamine in an aprotic solvent such as, but not limited to, dichloromethane, N,N-dimethylformamide or tetrahydrofuran at temperatures ranging from about −5° C. to about 50° C. to yield the intermediate acylated derivative (5). Subsequent coupling of the acyl chloride or acyl bromide of formula (5), where J is COCl or COBr, with an appropriately substituted primary or secondary amine of formula (3) in the presence of a stoichiometric amount of Hünig's base, in an aprotic solvent such as, but not limited to, dichloromethane, N,N-dimethylformamide or tetrahydrofuran, at temperatures ranging from about ambient to the reflux temperature of the solvent, provides the desired compounds of formula (I) wherein $R_1$, $R_2$, $R_3$ and B are as defined hereinbefore.

Alternatively, the acylating species can be a mixed anhydride of the corresponding carboxylic acid, such as, but not limited to, that prepared by treating said acid of formula (4) with 2,4,6-trichlorobenzoyl chloride in an aprotic organic solvent such as, but not limited to, dichloromethane according to the procedure of Inanaga et al., Bull. Chem. Soc. Jpn. 52, 1989 (1979). Treatment of said mixed anhydride of formula (5) with an appropriately substituted primary or secondary amine of formula (3) in an aprotic solvent such as, but not limited to, dichloromethane at temperatures ranging from about ambient to the reflux temperature of the solvent, provides the desired compounds of formula (I) wherein $R_1$, $R_2$, $R_3$ and B are as defined hereinbefore.

Alternatively, amidation of the carboxylic acids of formula (4) can be effectively carried out by treatment of said acid with triphosgene in an aprotic solvent such as, but not limited to, dichloromethane, followed by reaction of the activated intermediate with an appropriately substituted primary or secondary amine of formula (3) in the presence of an organic base such as, but not limited to, Hünig's base at temperatures ranging from about −10° C. to about ambient.

Another preferred process for the preparation of the compounds of the present invention of formula (I) wherein $R_1$, $R_2$, $R_3$ and B are as defined hereinbefore, consists of treating the acid of formula (4) with an activating reagent such as, but not limited to, N,N-dicyclohexylcarbodiimide or 1-ethyl-3-(3-dimethylamino-propyl)carbodiimide hydrochloride in the presence of 1-hydroxybenzotriazole, followed by reaction of the activated intermediate with an appropriately substituted primary or secondary amine of formula (3), preferably in the presence of an organic base such as, but not limited to, Hünig's base and a catalytic amount of 4-(dimethylamino)pyridine in an aprotic solvent such as, but not limited to, dichloromethane, N,N-dimethylformamide or tetrahydrofuran at temperatures ranging from about −10° C. to about ambient.

In another preferred process, said acid of formula (4) can be activated by treatment with other activating agents such as, but not limited to, N,N'-carbonyldiimidazole in an aprotic solvent such as, but not limited to, dichloromethane or tetrahydrofuran, at temperatures ranging from about −10° C. to the reflux temperature of the solvent. Subsequent reaction of the activated intermediate imidazolide with an appropriately substituted primary or secondary amine of formula (3) provides the desired compounds of formula (I) wherein $R_1$, $R_2$, $R_3$ and B are as defined hereinbefore.

Alternatively, the coupling of the appropriately substituted primary or secondary amine of formula (3) with said acid of formula (4) can be effectively carried out by using hydroxybenzotriazole tetramethyluronium hexafluorophosphate as the coupling reagent in the presence of an organic base such as, but not limited to, Hünig's base and in a solvent such as, but not limited to, N,N-dimethylformamide at temperatures ranging from about −10° C. to about ambient, to provide in good isolated yield and purity the desired compounds of formula (I) wherein $R_1$, $R_2$, $R_3$ and B are as defined hereinbefore.

Related coupling reagents such as, but not limited to, diphenylphosphoryl azide, diethyl cyano phosphonate, benzotriazol-1-yl-oxy-tris-(dimethylamino)phosphonium hexafluorophosphate and all other known in the literature that have been used in the formation of amide bonds in peptide synthesis can also be used for the preparation of compounds of formula (I) wherein $R_1$, $R_2$, $R_3$ and B are as defined hereinbefore.

The method used for the preparation of compounds of formula (I) from the intermediate carboxylic acid of formula (4) is ultimately chosen on the basis of its compatibility with the $R_1$, $R_2$, $R_3$ and B groups, and its reactivity with the tricyclic diazepine of formula (1).

Another preferred process for the preparation of (I) is shown in Scheme III. A tricyclic diazepine of formula (1) is reacted with diphosgene in an aprotic solvent such as, but not limited to, dichloromethane, preferably in the presence of an organic base such as, but not limited to, triethylamine, followed by reaction of the resulting acylated intermediate with an appropriately substituted primary or secondary amine of formula (3), to provide the desired compounds of formula (I) wherein $R_1$, $R_2$, $R_3$ and B are as defined hereinbefore.

can be conveniently prepared as shown in Scheme IV

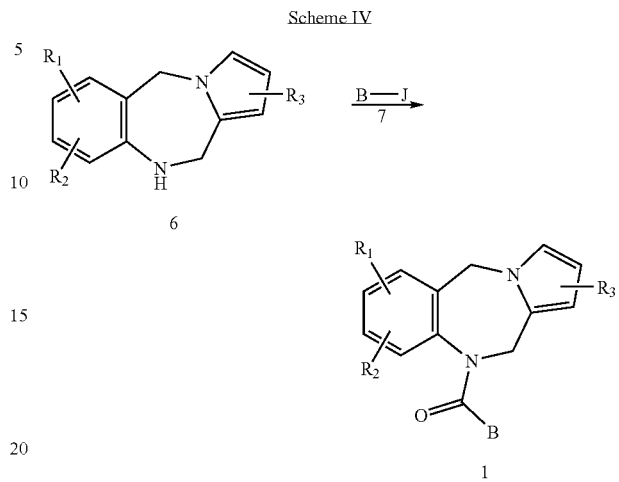

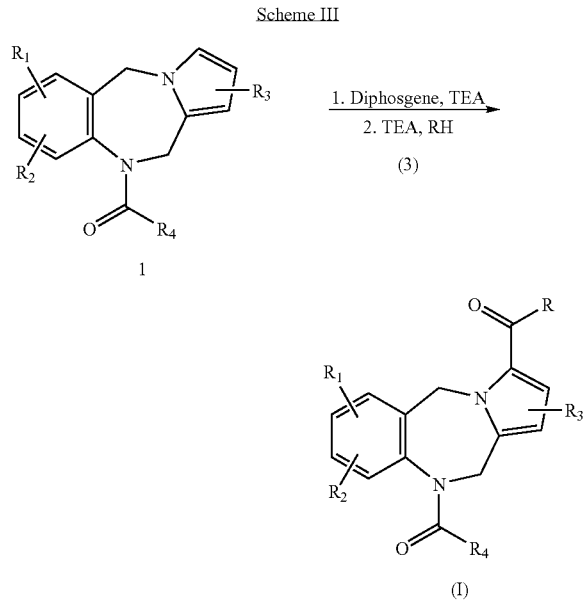

The tricyclic diazepines of formula (1) of Scheme I wherein B is

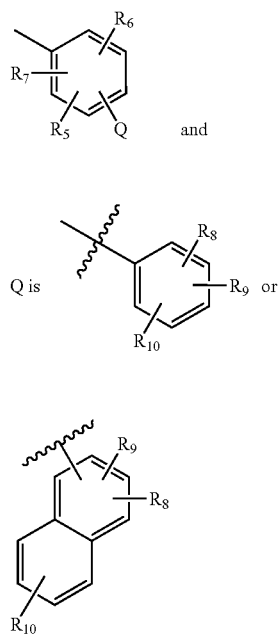

Thus, a tricyclic diazepine of formula (6) is treated with an appropriately substituted acylating agent such as, but not limited to, an aroyl halide, preferably an appropriately substituted acyl chloride or acylbromide of formula (7), where J is COCl or COBr, wherein B is ultimately chosen on the basis of its compatibility with the present reaction scheme, in the presence of an inorganic base such as, but not limited to, potassium carbonate, or in the presence of an organic base such as, but not limited to, pyridine, 4-(dimethylamino)pyridine, or a tertiary amine such as, but not limited to, triethylamine, N,N-diisopropylethyl amine or N,N-dimethylaniline, in an aprotic solvent such as, but not limited to, dichloromethane, N,N-dimethylformamide, tetrahydrofuran or 1,4-dioxane, at temperatures ranging from about −5° C. to about 50° C. to provide intermediates of general formula (1).

Alternatively, the acylating species of formula (7) can be a mixed anhydride of the corresponding carboxylic acid, such as, but not limited to, that prepared by treating said acid with 2,4,6-trichlorobenzoyl chloride in an aprotic organic solvent such as, but not limited to, dichloromethane according to the procedure of Inanaga et al., Bull. Chem. Soc. Jpn., 52, 1989 (1979). Treatment of said mixed anhydride of general formula (7) with a tricyclic diazepine of formula (6) in a solvent such as, but not limited to, dichloromethane, and in the presence of an organic base such as, but not limited to, 4-(dimethylamino)pyridine, at temperatures ranging from about 0° C. to the reflux temperature of the solvent, yields the intermediate acylated derivative of formula (1) of Scheme IV.

The acylating intermediate of formula (7) is ultimately chosen on the basis of its compatibility with the B groups, and its reactivity with the tricyclic diazepine of formula (6).

The desired intermediates of formula (7) of Scheme IV wherein B is (a) can be conveniently prepared by a process shown in Scheme V. Thus, an appropriately substituted aryl iodide, aryl bromide, aryl chloride, or aryl trifluoromethane sulfonate of formula (8), wherein Pg is a carboxylic acid protecting group, preferably Pg is alkyl or benzyl, M is I, Br, Cl, OTf, and $R_5$, $R_6$ and $R_7$ are defined hereinbefore, is reacted with an aryl tri(alkyl)tin(IV) derivative of formula (9), where T is Sn(alkyl)$_3$, preferably Sn(n-Bu)$_3$) wherein $R_8$, $R_9$ and $R_{10}$ are defined hereinbefore, in the presence of a Pd(0) catalyst, and in the presence or absence of inorganic salts (e.g. LiCl or copper(I) salts) to provide the intermediate ester of formula (10). Subsequent unmasking of the carboxylic function by hydrolysis, hydrogenolysis or similar methods known in the art, followed by activation of the intermediate acid of formula (11) provides the desired compounds of formula (7) wherein $R_5$, $R_6$, $R_7$, $R_8$, $R_9$ and $R_{10}$ are hereinbefore defined, suitable for coupling with the tricyclic diazepine of formula (6).

rabutylammonium iodide, in a mixture of solvents such as, but not limited to, toluene-ethanol-water, acetone-water, water or water-acetonitrile, at temperatures ranging from about ambient to the reflux temperature of the solvent (Suzuki, Pure & Appl. Chem. 66, 213-222 (1994), Badone et al.,

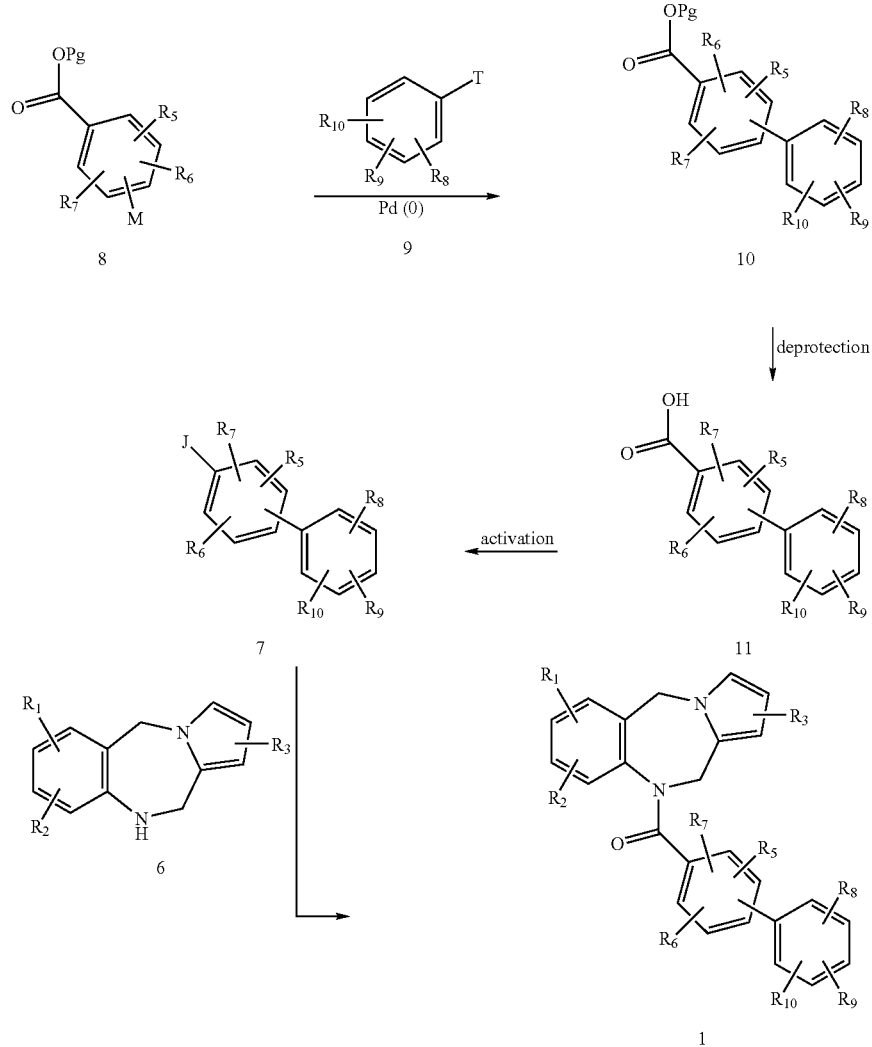

The desired intermediates of formula (7) of Scheme IV wherein Q is (b) can be prepared by a process analogous to that exemplified in Scheme V by replacing intermediates of formula (9) with appropriately substituted naphthyl intermediates.

Alternatively, the desired intermediates of formula (10) of Scheme V wherein Q is (a) can be prepared by coupling of the iodide, bromide, chloride, or trifluoromethane sulfonate of formula (8), where M is I, Br, Cl or OTf, with an appropriately substituted aryl boron derivative of formula (9), where preferably T is B(OH)$_2$, in the presence of a palladium catalyst such as, but not limited to, palladium(II) acetate or tetrakis (triphenylphosphine)palladium(0) and an organic base such as, but not limited to, triethylamine or an inorganic base such as, but not limited to, sodium, potassium, or cesium carbonate with or without added tetrabutylammonium bromide or tet- J. Org. Chem. 62, 7170-7173 (1997), Wolfe et al. J. Am. Chem. Soc. 121, 9559 (1999), Shen, Tetr. Letters 38, 5575 (1997)). The exact conditions for the Suzuki coupling of the halide and the boronic acid intermediates are chosen on the basis of the nature of the substrate and the substituents. The desired intermediates of formula (10) of Scheme V can be similarly prepared from the bromide of formula (8), where M is Br, and the boronic acid of formula (9) in a solvent such as, but not limited to, dioxane in the presence of potassium phosphate and a Pd(0) catalyst.

Alternatively, a palladium-catalyzed cross-coupling reaction of an aryl halide, or trifluoromethane sulfonate of formula (9), where T is Br, I or OTf, with a pinacolato derivative of formula (8), where M is

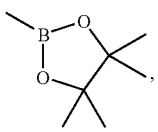

B(OH)$_2$, or SnBu$_3$) yields the desired intermediate of formula (10) which is converted to a compound of formula (1) in the manner of Scheme V.

The desired intermediates of formula (10) of Scheme V wherein Q is (b) can be prepared in analogous fashion by replacing intermediates of formula (9) with appropriately substituted naphthyl intermediates.

The required appropriately substituted aryl halides of formula (8), where M is Br or I, of Scheme V are either available commercially, or are known in the art, or can be readily accessed in quantitative yields and high purity by diazotization of the corresponding substituted anilines of formula (8), where Pg is H, alkyl or benzyl, and M is NH$_2$, followed by reaction of the intermediate diazonium salt with iodine and potassium iodide in aqueous acidic medium essentially according to the procedures of Street et al., J. Med. Chem. 36, 1529 (1993) and Coffen et al., J. Org. Chem. 49, 296 (1984) or with copper(I) bromide, respectively (March, Advanced Organic Chemistry, 3$^{rd}$ Edn., p. 647-648, John Wiley & Sons, New York (1985)).

Alternatively, the desired intermediates of formula (11) of Scheme V wherein Q is (a) can be conveniently prepared as shown in Scheme VI by cross-coupling reaction of an appropriately substituted pinacolato boronate of formula (13) wherein R$_8$, R$_9$ and R$_{10}$ are hereinbefore defined, with an aryl triflate of formula (14), where W is OTf, or an aryl halide where the halide Br, or I, wherein R$_5$, R$_6$ and R$_7$ are defined hereinbefore, according to the general procedures of Ishiyama et al., Tetr. Lett. 38, 3447-3450 (1997) and Giroux et al. Tetr. Lett. 38, 3841-3844 (1997), followed by basic or acidic hydrolysis of the intermediate nitrile of formula (15) (cf. March, Advanced Organic Chemistry, 3$^{rd}$ Edn., John Wiley & Sons, New York, p. 788 (1985)).

Scheme VI

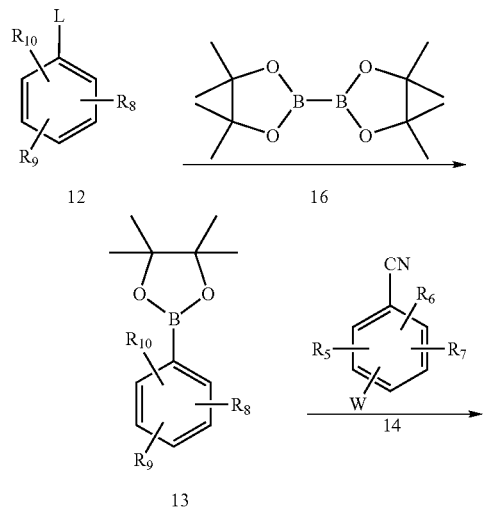

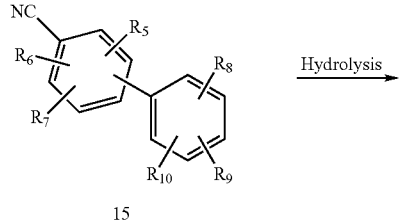

Hydrolysis

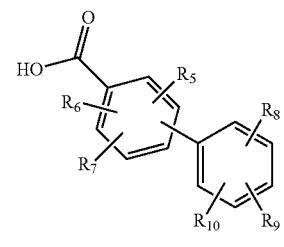

Alternatively, reaction of an iodide, bromide, chloride, or trifluoromethane sulfonate of formula (12), where L is Br, Cl, I, or OTf, with a boronic acid or trialkyl tin(IV) derivative of formula (14), where W is B(OH)$_2$, or SnBu$_3$, yields the desired intermediate of formula (15) which is converted to a compound of formula (11) in the manner of Scheme VI.

The desired intermediates of formula (15) of Scheme VI where Q is (b) can be prepared in analogous fashion by replacing intermediates of formulas (13) with appropriately substituted naphthyl intermediates.

The desired phenyl boronic esters of formula (13) of Scheme VI can be conveniently prepared by the palladium-catalyzed cross-coupling reaction of bis(pinacolato)diboron of formula (16) with an appropriately substituted aryl halide of formula (12), preferably a bromide or iodide, where L is Br, I, or an aryl triflate, where L is OTf, according to the published procedures of Ishiyama et al., J. Org. Chem. 60, 7508-7510 (1995) and Giroux et al., Tetr. Lett. 38, 3841-3844 (1997).

The desired compounds of formula (1) of Scheme IV wherein Q is (a) can be alternatively prepared by a process shown in Scheme VII.

Scheme VII

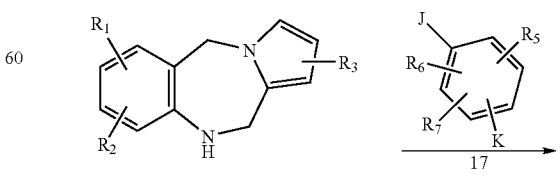

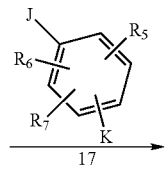

-continued

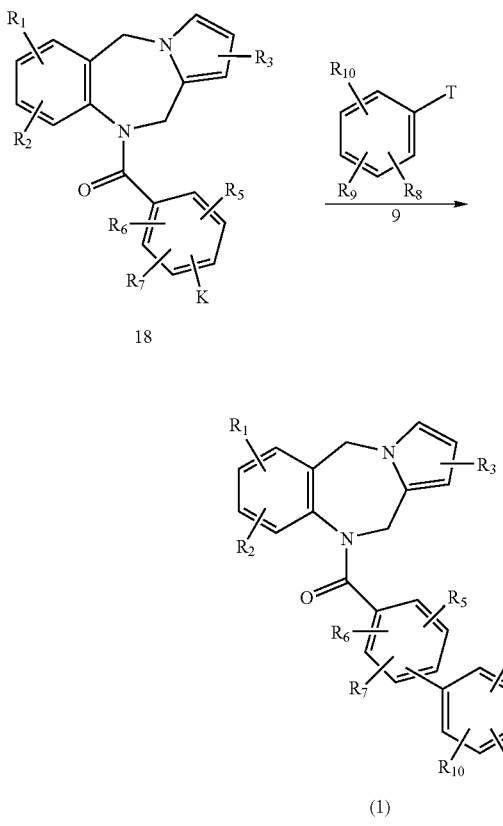

(1)

Thus, a tricyclic diazepine of formula (6) is treated with an appropriately substituted acylating agent such as, but not limited to, a halo aroyl halide, preferably an iodo aroyl chloride or bromo aroyl bromide of formula (17), where J is COCl or COBr; and K is I, Br, wherein $R_5$, $R_6$ and $R_7$ are hereinbefore defined, using any of the procedures hereinbefore described, to provide the acylated intermediate of general formula (18) of Scheme VII.

Alternatively, the acylating species of formula (17) can be a mixed anhydride of the corresponding carboxylic acid. Treatment of said mixed anhydride of general formula (17) with a tricyclic diazepine of formula (6) according to the procedure described hereinbefore yields the intermediate acylated derivative of formula (18).

The acylating intermediate of formula (17) is ultimately chosen on the basis of its compatibility with the $R_5$, $R_6$ and $R_7$ groups, and its reactivity with the tricyclic diazepine of formula (6).

A Stille coupling reaction of a compound of formula (18), where K is I, with an appropriately substituted organotin reagent such as, but not limited to, a trialkyltin(IV) derivative, preferably a tri-n-butyltin(IV) derivative of formula (9), where T is $SnBu_3$, where $R_8$, $R_9$ and $R_{10}$ are hereinbefore defined, in the presence of a catalyst such as, but not limited to, tetrakis(triphenylphosphine)palladium (0), in an aprotic organic solvent such as, but not limited to, toluene and N,N-dimethylformamide, at temperatures ranging from about ambient to about 150° C. (cf. Farina et al., J. Org. Chem, 59, 5905 (1994) and references cited therein), affords the desired compounds of formula (1) wherein $R_1$, $R_2$, $R_3$, $R_5$, $R_6$, $R_7$, $R_8$, $R_9$ and $R_{10}$ are as defined hereinbefore.

Alternatively, reaction of a compound of formula (18), where K is Cl, Br or I, with an appropriately substituted aryl boronic acid of formula (9), where T is $B(OH)_2$, wherein $R_5$, $R_6$, $R_7$, $R_8$, $R_9$ and $R_{10}$ are hereinbefore defined, in a mixture of solvents such as, but not limited to, toluene-ethanol-water, in the presence of a Pd(0) catalyst and a base such as, but not limited to, sodium carbonate, at temperatures ranging from about ambient to the reflux temperature of the solvent, yields the desired compounds of formula (1) wherein $R_1$, $R_2$, $R_3$, $R_5$, $R_6$, $R_7$, $R_8$, $R_9$ and $R_{10}$ are as defined hereinbefore.

The preferred substituted aroyl chlorides(bromides) of formula (17) of Scheme VII, where K is I, Br; and J is COCl or COBr, wherein $R_5$, $R_6$ and $R_7$ are as defined hereinbefore, are either available commercially, or are known in the art, or can be readily prepared by procedures analogous to those in the literature for the known compounds.

The intermediates of formula (9), where T is $Sn(alkyl)_3$, and alkyl is preferably n-butyl, of Scheme VII are either commercially available, or can be conveniently prepared as shown in Scheme VIII from the corresponding bromo starting materials of formula (19) wherein $R_8$, $R_9$, and $R_{10}$ are hereinbefore defined, by first reacting them with n-butyl lithium followed by reaction of the intermediate lithiated species with a trialkyl (preferably trimethyl or tri-n-butyl)tin(IV) chloride, preferably trimethyl tin(IV) chloride or tri-n-butyl tin(IV) chloride.

Scheme VIII

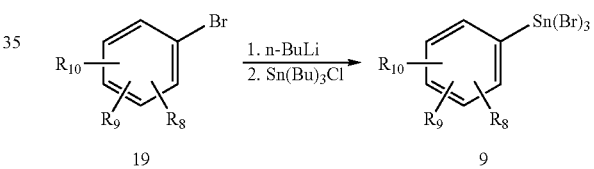

The preferred substituted aryl boronic acids of formula (9), where T is $B(OH)_2$, are either available commercially, or are known in the art, or can be readily prepared by procedures analogous to those in the literature for the known compounds.

The desired compounds of formula (1) of Scheme VII wherein B is (b) can be prepared in analogous fashion by replacing intermediates of formula (9) with appropriately substituted naphthyl intermediates.

Alternatively, as shown in Scheme IX, the appropriately substituted aroyl halides, preferably aroyl chlorides of formula (20) where J=COCl, where $R_5$, $R_6$ and $R_7$ are hereinbefore defined, are reacted with a tricyclic diazepine of formula (6) to provide the intermediate bromides of formula (21). Subsequent reaction of (21) with an hexa alkyl-di-tin (preferably hexa-n-butyl-di-tin(IV)) in the presence of a Pd(0) catalyst such as tetrakis(tri-phenylphosphine)palladium(0) and lithium chloride or copper(I) salts, provides the stannane intermediate of formula (22). Further reaction of the tri-n-butyl tin(IV) derivative (22) with the appropriately substituted aryl halide of formula where 23, M=bromo or iodo, wherein $R_8$, $R_9$, and $R_{10}$ are hereinbefore defined, in the presence of a Pd(0) catalyst such as tetrakis(triphenylphosphine)palladium(0), yields the desired compounds of formula (1) wherein Q is (a), and $R_1$, $R_2$, $R_3$, $R_5$, $R_6$, $R_7$, $R_8$, $R_9$ and $R_{10}$ are defined hereinbefore.

Scheme IX

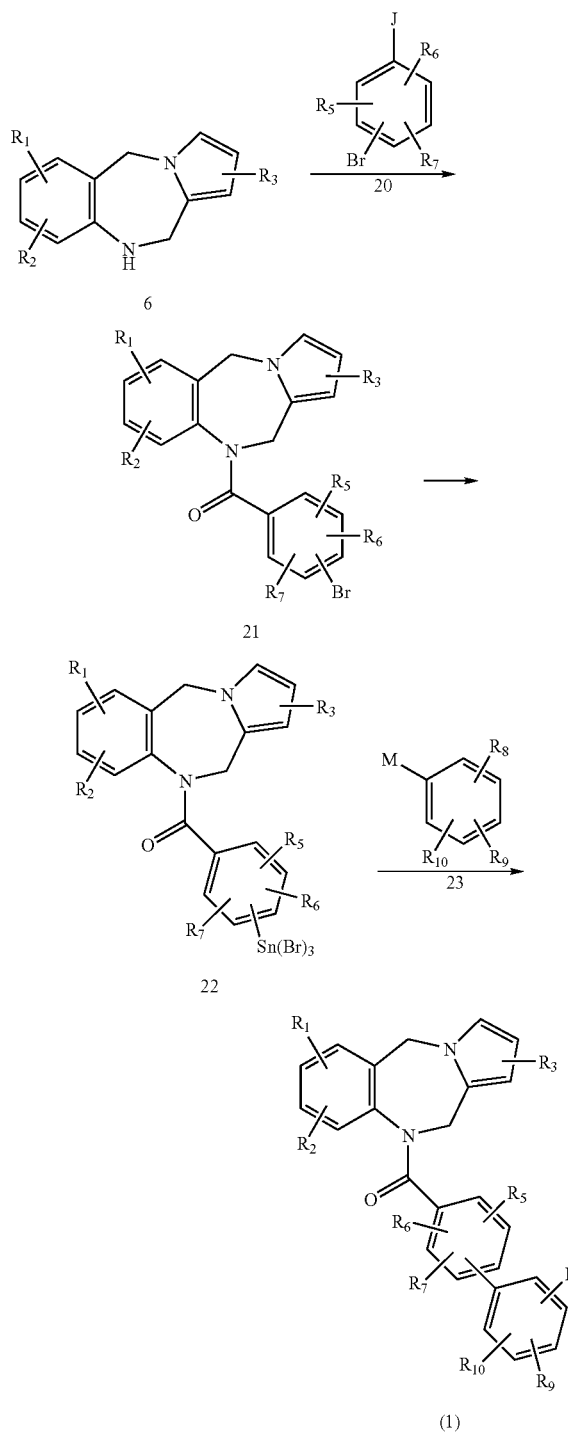

Scheme X

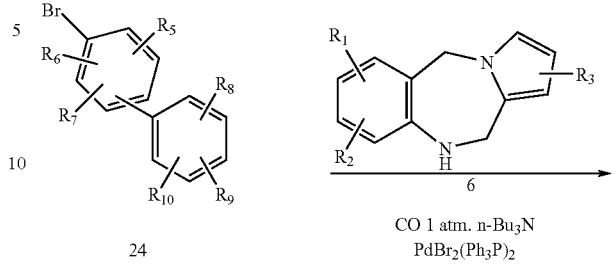

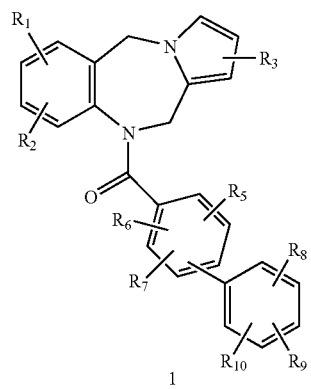

Thus, an appropriately substituted biphenyl of formula (24) wherein $R_5$, $R_6$, $R_7$, $R_8$, $R_9$ and $R_{10}$ are defined hereinbefore, is treated with carbon monoxide in the presence of a tricyclic diazepine of formula (6), a palladium(0) catalyst preferably $PdBr_2(Ph_3P)_2$ and a tertiary amine preferably n-tributylamine, in a solvent such as, but not limited to, anisole or dioxane, at temperatures ranging from about ambient to the reflux temperature of the solvent (cf. Schoenberg et al. J. Org. Chem. 39, 3327 (1974)) to provide the desired compounds of formula (1) wherein $R_1$, $R_2$, $R_3$, $R_5$, $R_6$, $R_7$, $R_8$, $R_9$ and $R_{10}$ are defined hereinbefore.

In analogous fashion one can prepare compounds of formula (1) of Scheme X wherein Q is (b) provided that the intermediates of formula (24) are replaced by the appropriately substituted naphthyl intermediates.

A preferred process for the preparation of the desired compounds of general formula (I) of Scheme I wherein B is selected from the group (a) or (b) defined hereinbefore is shown in Scheme XI The desired compounds of formula (1) of Scheme IX wherein Q is (b) can be prepared in analogous fashion by replacing intermediates of formula (23) with appropriately substituted naphthyl intermediates.

Alternatively, the desired compounds of formula (1) of Scheme IX wherein Q is (a) can be prepared as shown in Scheme X.

Scheme XI

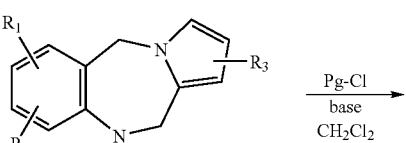

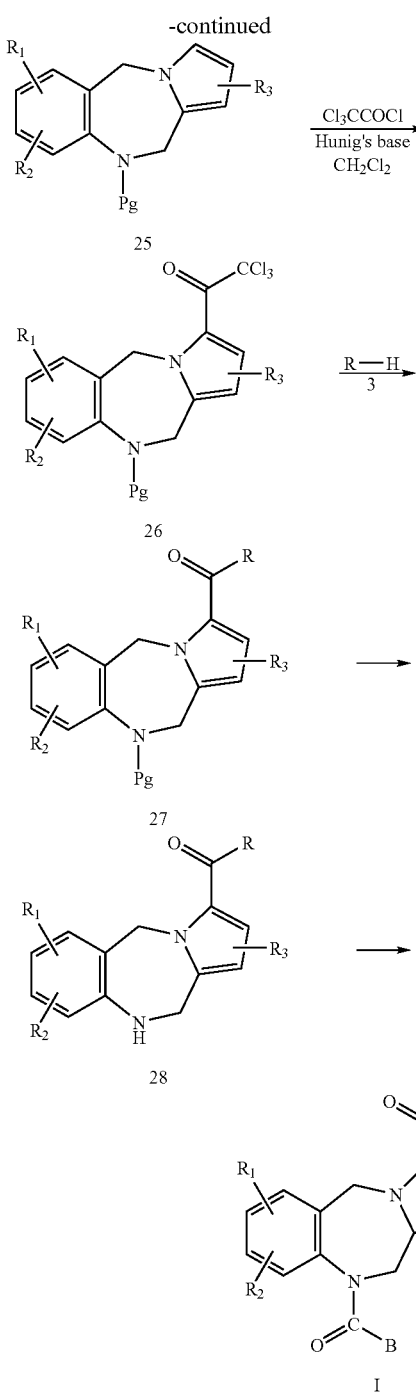

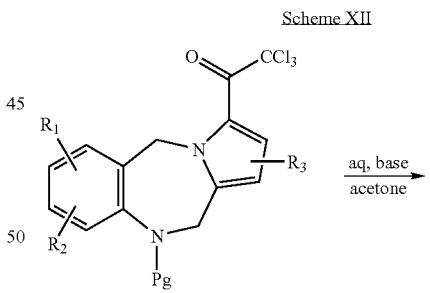

dichloromethane, at temperatures ranging from about −10° C. to about ambient to provide the desired trichloroacetyl intermediate of formula (26). Subsequent reaction with a primary or secondary amine of formula (3) under the conditions of Scheme I yields the intermediate amide of formula (27) where Pg is Boc, which is then deprotected (intermediate 28) and acylated to the desired product of formula (I). Alternatively, the conversion of (26) to the intermediate of formula (28) can be carried out in a single step by treatment of the intermediate of formula (26) where Pg is Fmoc, with a primary amine of formula (3) in the presence of dimethylsulfoxide in an aprotic solvent such as, but not limited to, acetonitrile, at reflux temperature of the solvent.

Alternatively, hydrolysis of the trichloroacetate intermediate (26) with aqueous base such as, but not limited to, sodium hydroxide in an organic solvent such as, but not limited to, acetone, at temperatures ranging from about −10° C. to about ambient, is accompanied by simultaneous removal of the protecting group (Pg is Fmoc) and yields the intermediate acid of formula (29) as shown in Scheme XII. The required amidation of the carboxylic acid of formula (29) can be effectively accomplished by treating the carboxylic acid of formula (29) with an activating reagent such as, but not limited to, N,N-dicyclohexylcarbodiimide or 1-ethyl-3-(3-dimethylamino-propyl)carbodiimide hydrochloride in the presence of 1-hydroxybenzotriazole, followed by reaction of the activated intermediate with an appropriately substituted primary or secondary amine of formula (3) preferably in the presence of Hünig's base or a catalytic amount of 4-(dimethylamino)pyridine, in an aprotic solvent such as, but not limited to, dichloromethane, N,N-dimethylformamide or tetrahydrofuran, at temperatures ranging from about −10° C. to about ambient. Subsequent acylation of the amide of formula (28) under the conditions of Scheme IV provides the desired compounds of formula (I).

Scheme XII

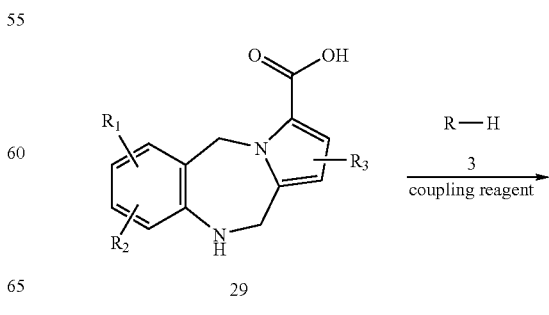

Thus, a tricyclic diazepine of formula (25) wherein $R_1$, $R_2$ and $R_3$ are defined hereinbefore, carrying a protecting group (Pg) such as, but not limited to, fluorenylalkoxycarbonyl group, preferably a fluorenylmethyloxycarbonyl (Pg is Fmoc) group, or an alkoxycarbonyl protecting group preferably a tert-butyloxycarbonyl (Pg is Boc) group is reacted with a perhaloalkanoyl halide preferably trichloroacetyl chloride, in the presence of an organic base such as, but not limited to, N,N-diisopropylethyl amine (Hünig's base) or a tertiary amine such as, but not limited to, triethylamine, optionally in the presence of catalytic amounts of 4-(dimethylamino)pyridine, in an aprotic organic solvent such as, but not limited to,

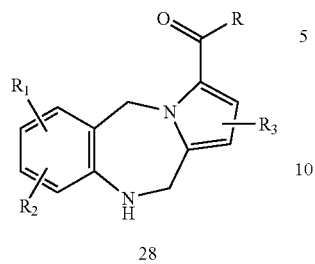

28

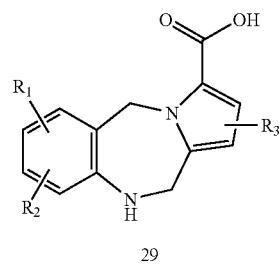

29

Other coupling reagents known in the literature that have been used in the formation of amide bonds in peptide synthesis can also be used for the preparation of compounds of formula (28). The method of choice for the preparation of compounds of formula (28) from the intermediate carboxylic acid of formula (29) is ultimately chosen on the basis of its compatibility with the $R_1$, $R_2$, and $R_3$ groups.

Alternatively, the intermediate acids of formula (29) of Scheme XII wherein $R_1$, $R_2$, and $R_3$ are defined hereinbefore, can be obtained by reacting a tricyclic diazepine of formula (6) with an excess of acylating agent preferably trifluoroacetic anhydride or trichloroacetyl chloride in the presence of an inorganic base such as, but not limited to, potassium carbonate or an organic base such as, but not limited to, N,N-diisopropylethylamine, in an aprotic solvent such as, but not limited to, N,N-dimethylformamide, followed by basic hydrolysis of the intermediate bis-trifluoroacetyl(trichloroacetyl) intermediate of formula (30) preferably with aqueous sodium hydroxide in a protic organic solvent such as, but not limited to, ethanol, at temperatures ranging from about ambient to the reflux temperature of the solvent as exemplified in Scheme XIII.

Preferred processes for the preparation of compounds of formula (I) of Scheme I wherein Q is (a), and $R_1$, $R_2$, $R_3$, $R_5$, $R_6$, $R_7$, $R_8$, $R_9$, and $R_{10}$ are defined hereinbefore, also utilize acylation of the intermediate (28) of Scheme XII with an acylating agent of formula (17) of Scheme VII, as shown in Scheme XIV. Subsequent coupling of the intermediate of formula (31), where K is Br or I, with an appropriately substituted aryl boronic acid of formula (9), where T is $B(OH)_2$, in a mixture of solvents such as, but not limited to, dimethoxyethane and water or acetonitrile and water, in the presence of a Pd(O) catalyst such as, but not limited to, tetrakis(triphenylphosphine)palladium(0) or a Pd(II) catalyst such as, but not limited to, [1,1'-bis(diphenylphosphino)ferrocene] dichloro palladium(II), and a base such as, but not limited to, potassium or sodium carbonate, at temperatures ranging from about ambient to reflux, yields the desired compound (I).

Scheme XIII

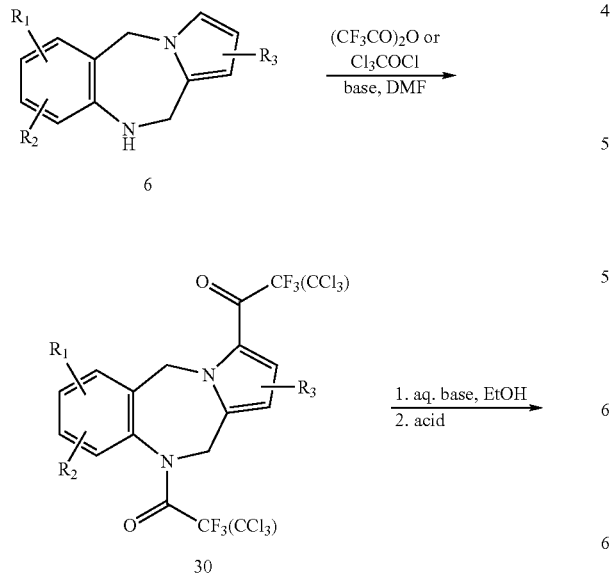

Scheme XIV

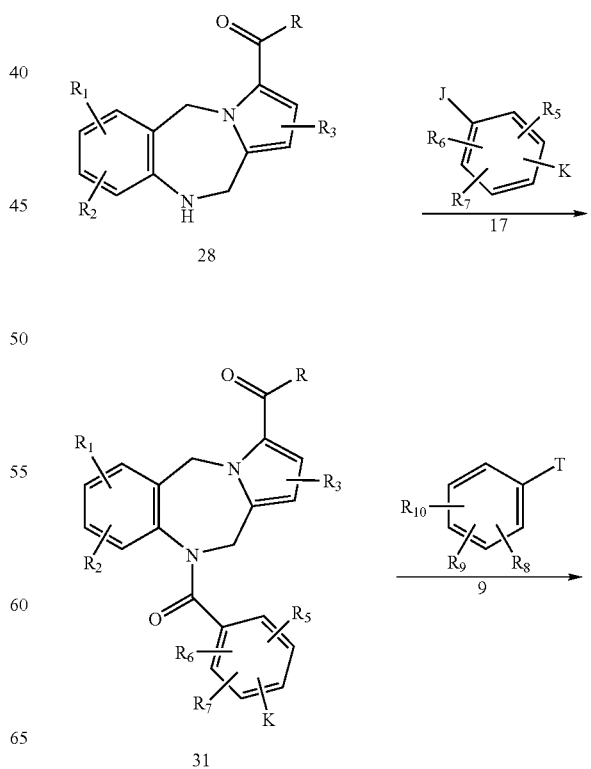

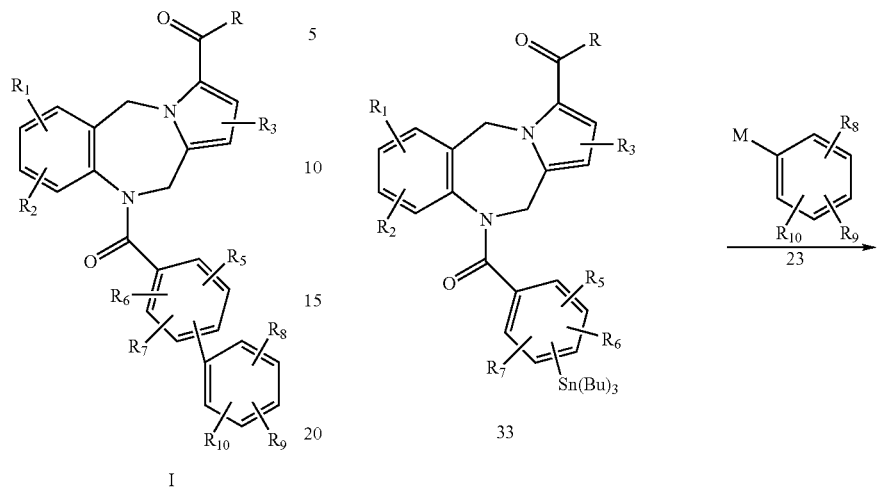

I

Alternatively, the preferred compounds of formula (I) of Scheme I wherein Q is (a) and $R_1$, $R_2$, $R_3$, $R_5$, $R_6$, $R_7$, $R_8$, $R_9$, and $R_{10}$ are defined hereinbefore, can be prepared as shown in Scheme XV by acylation of the intermediate (28) of Scheme XII with an acylating agent of formula (20) of Scheme IX.

Scheme XV

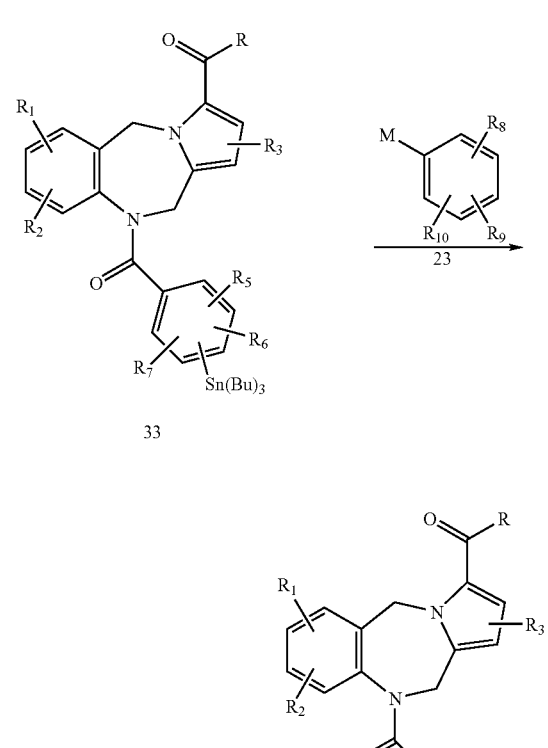

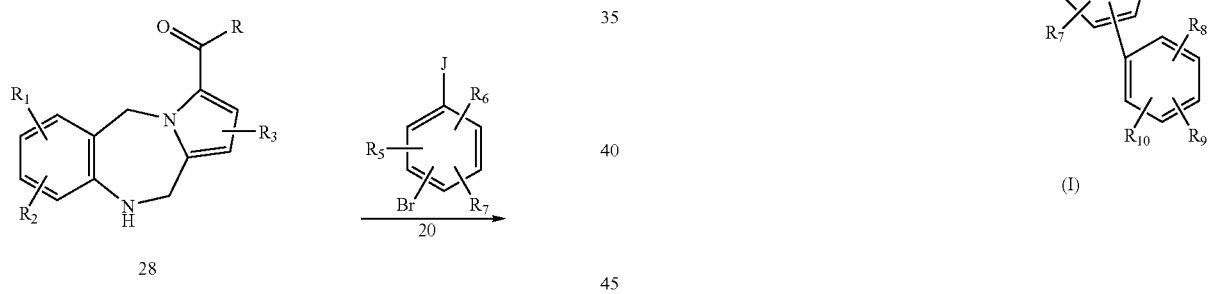

(I)

Alternatively, the preferred compounds of formula (I) of Scheme (I) wherein Q is (a) and $R_1$, $R_2$, $R_3$, $R_5$, $R_6$, $R_7$, $R_8$, $R_9$, and $R_{10}$ are defined hereinbefore, can be prepared by acylation of the amide intermediate of formula (28) of Scheme XII with an acylating agent of formula (7) of Scheme V, wherein J is hereinbefore defined, as shown in Scheme XVI.

Scheme XVI

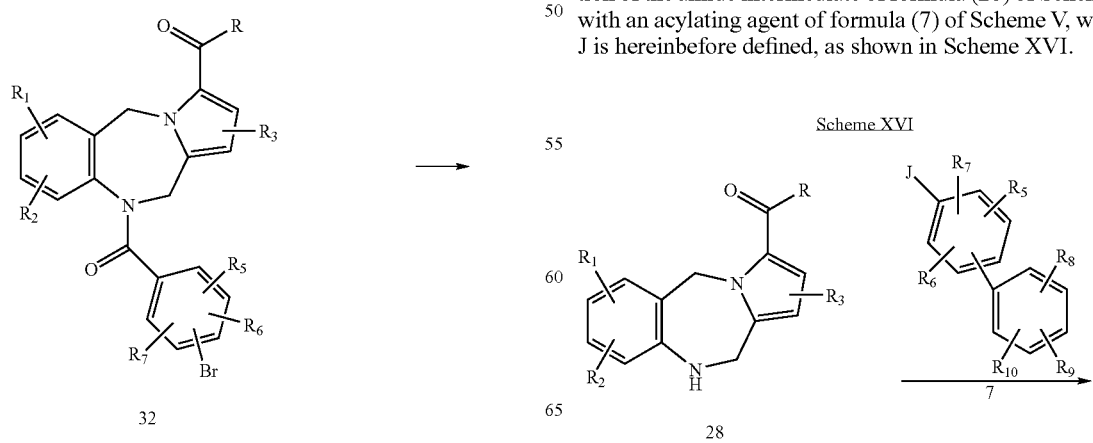

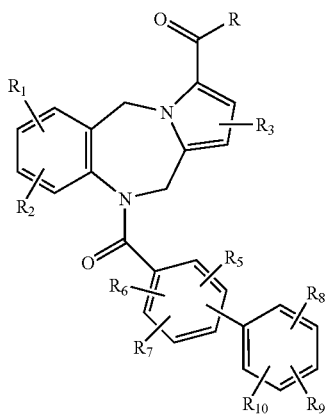

(I)

A preferred process for the preparation of the amide intermediate of formula (31) of Scheme XIV is shown in Scheme XVII. A tricyclic benzodiazepine of formula (6) is acylated with an acylating agent of formula (17), where K is Br or I, to provide the intermediate of formula (34). This is in turn, is reacted with a perhaloalkanoyl halide preferably trichloroacetyl chloride, under the conditions of Scheme I to provide the trichloroacetyl intermediate of formula (35). Subsequent reaction of the intermediate of formula (35) with an appropriate primary or secondary amine also under the conditions of Scheme I provides the desired product of formula (31).

Scheme XVII

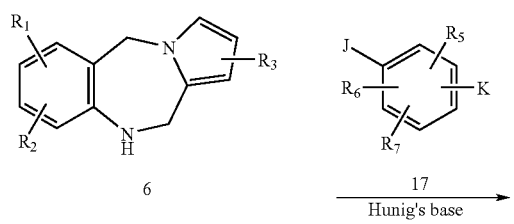

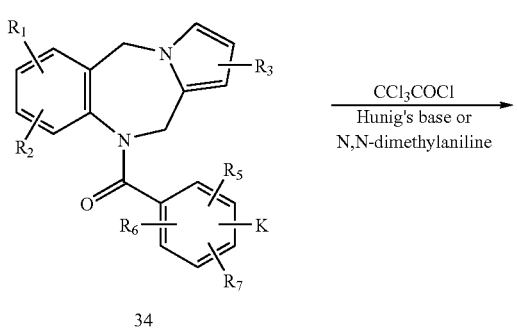

Brief Description of Biological Test Procedure(s) and Text Summary of Results

Pharmacology

The FSH antagonist activities of the compounds of this invention were demonstrated by evaluating representative compounds of this invention in the following test procedures.

Follicle-Stimulating Hormone Receptor-Dependent Cre-Luciferase Reporter Gene Assay for the Identification of Follicle-Stimulating Hormone (FSH) Antagonists This procedure was used to identify and determine the relative potencies of human FSH receptor antagonists using a Chinese hamster ovarian cell line that stably produces the human FSH receptor and a luciferase reporter gene regulated by cAMP response elements.

Materials and Methods: Reagents

COMPOUND VEHICLE: Stock compounds were solubilized in an appropriate vehicle, preferably phosphate buffered saline (PBS) or dimethyl sulfoxide (DMSO), at 30 mM. The compounds were subsequently diluted in DMSO to working dilutions of 1 and 20 or 30 mM for 2-dose testing format and 1 μM-10 mM for dose-response format. The DMSO dilutions were diluted 500-fold in sterile growth medium [D-MEM/F-12 (GIBCO/BRL; Grand Island N.Y.) containing 15 mM HEPES, 2 mM 1-glutamine, pyridoxine hydrochloride, phenol red and 5% FetalClone II (HyClone Laboratories, Inc; Logan, Utah), 0.2% DMSO, 100 units penicillin G/ml, and 100 μg streptomycin sulfate/ml (GIBCO/BRL)]. The concentration of the vehicle in each of the compound dilutions was the same.

POSITIVE CONTROLS: Purified human FSH (>98%) was purchased from Cortex Biochem, Inc. (San Leandro, Calif.) and a known FSH-R thiazolidinone antagonist was obtained from the Wyeth Research compound repository.

Preparation of Cells

The CHO FSH-R 6CRE-Luc cells (1D7 cells) were obtained from Affymax (Palo Alto, Calif.). These Chinese hamster ovary cells (CHO-K1) were genetically engineered to stably express the recombinant human FSH receptor gene and a luciferase reporter gene under the regulation of 6 copies of a cAMP response element. The cells were plated one day prior to treatment into 96-well white opaque plates at a density of 50,000 cells/100 µl/well in growth medium. On the day of treatment, the growth medium was removed from the wells by aspiration and 50 µl of fresh growth medium was added to each well. The cells were incubated at 37° C. in a humidified incubator with 5% $CO_2$/95% air.

Assay

Test compounds diluted to 2x final concentration in growth medium containing 2x EC50 purified human FSH (0.8 ng/ml) were added to the wells to achieve a final volume of 100 µl of medium containing 0.25% (v/v) vehicle. The treated cells were incubated for 4 hours at 37° C. in a humidified incubator with 5% $CO_2$/95% air. At the end of the incubation period, luciferase activity was measured by chemiluminescence using a commercially available kit (LucScreen, Tropix, Inc., Bedford, Mass.) according to the manufacturer's specifications, except that Buffer 1 and Buffer 2 were mixed together in equal proportion prior to the addition of 100 µl of the combined reagents to each well. Chemiluminescence was detected using a luminometer (EG & G Berthold Microlumat LB 96 P, Wallac, Gaithersburg, Md.) with chemiluminescence measured for 1 sec/well.

Background luminescence was measured for each well prior to the addition of the LucScreen reagent.

Experimental Groups

In the 96-well 2-dose format, each compound was tested in duplicate at each dose. The controls were also tested in duplicate on each plate and consisted of vehicle control and 3 positive controls ($EC_{50}$ of phFSH (0.4 ng/ml), $EC_{100}$ of phFSH (1000 ng/ml), and $IC_{50}$ of 3-[(2S*,5R*)-5-{[2-(1H-Indol-3-yl)-ethylcarbamoyl]-methyl}-4-oxo-2-(5-phenyl-ethynyl-thiophen-2-yl)-thiazolidin-3-yl]-benzamide (2 µM) in the presence of $EC_{50}$ of purified human FSH). One plate was used to test a maximum of 22 compounds.

In the 96-well dose-response format, each compound was tested in triplicate at each of 6 doses in the presence of the $EC_{50}$ of purified human FSH. The $EC_{50}$ of purified human FSH alone was tested in triplicate with each test compound. The doses chosen to test each compound were extrapolated from the initial 2-dose screening process. Along with the test compounds, purified human FSH was also tested in a dose response (0.03, 0.1, 0.3, 1, 3, 10, and 30 ng/ml) for a positive control and quality control. One plate was used for 3 test compounds and the FSH positive control.

Analysis of the Results

Luciferase activity is expressed as relative light units/sec/well. Luciferase activity in antagonist was compared to the appropriate negative and positive controls. For 2-dose testing, results are reported as luciferase activity and are expressed as % inhibition of the response obtained from the $EC_{50}$ of FSH. For dose-response testing, results are reported as $IC_{50}$ values. Data were analyzed statistically by one-way analysis of variance with appropriate weighting and transformation and relevant paired test as determined by Biometrics (Wyeth Research, Princeton, N.J.). $IC_{50}$ values were calculated using the Stat/Excel program developed by Biometrics with appropriate weighting and transformation.

Reference Compounds

Test compounds were compared to the effect of purified human FSH and 3-[(2S*,5R*)-5-{[2-(1H-Indol-3-yl)-ethylcarbamoyl]-methyl}-4-oxo-2-(5-phenylethynyl-thiophen-2-yl]-thiazolidin-3-yl]-benzamide in 2-dose format and $EC_{50}$ concentration of purified human FSH in dose-response format.

REFERENCES

1. Kelton, C. A., Cheng, S. V. Y., Nugent, N. P., Schweickhardt, R. L., Rosenthal, J. L., Overton, S. A., Wands, G. D., Kuzeja, J. B., Luchette, C. A., and Chappel, S. C. (1992). The cloning of the human follicle stimulating hormone receptor and its expression in COS-7, CHO, and Y-1 cells. Mol. Cell. Endocrinol. 89:141-151.
2. Tilly, J. L., Aihara, T., Nishimori, K., Jia, X.-C., Billig, H., Kowalski, K. I., Perlas, E. A., and Hsueh, A. J. W. (1992). Expression of recombinant human follicle-stimulating hormone receptor: Species-specific ligand binding, signal transduction, and identification of multiple ovarian messenger ribonucleic acid transcripts. Endocrinology 131: 799-806.
3. George, S. E., Bungay, P. J., and Naylor, L. H. (1997). Evaluation of a CRE-directed luciferase reporter gene assay as an alternative to measuring cAMP accumulation. J. Biomol. Screening 2:235-240.

In Vitro Bio-Assay of Agonists and Antagonists to the FSH Receptor Selectivity and Dependency of Agonists and Antagonists to the FSH Receptor This assay was used to verify in vitro potency, efficacy, selectivity and receptor dependency of hits found to inhibit an FSH-R-CRE-luciferase driven reporter.

Methods: Reagants

COMPOUND VEHICLE: Stock compounds were solubilized in 100% DMSO (Sigma Chemical Co.) at a concentration of 30 mM. The compounds were subsequently diluted in sterile assay medium consisting of Opti-MEM® I (Life Technologies) with 0.1% (w/v) BSA (Sigma), prior to use in the bio-assay. The final concentration of DMSO in the assay is 0.1%.

Preparation of CHO-3D2 Cells

The day prior to the experiment, CHO-3D2 cells (hFSH-R)(1) were plated into 96-well tissue culture plates (Falcon) at a density of 30,000 cells/well in DMEM/F12 medium (Life Technologies) supplemented with 5% Fetal Clone II (Hyclone), 2 mM L-glutamine (Life Technologies) and penicillin/streptomycin (100 U/ml, Life Technologies). Plated cells are then incubated at 37° C. in a humidified 5% $CO_2$/95% air, atmosphere.

Assay:

On the day of the assay, cells were washed three times with 100 µl/well of assay medium consisting of Opti-MEM® I (Life Technologies) with 0.1% (w/v) BSA (Sigma). Medium was removed and 100 µl of assay medium was added to each well. Plates were incubated for an additional 30 minutes at 37° C. Medium was then removed and cells were challenged for 30 minutes at 37° C. in 50 µl of assay media containing vehicle, purified hFSH (>95% pure; Cortex Biochem, Inc., San Leandro, Calif.) in the presence or absence of test compounds. Reactions were terminated by the addition of 50 µl of 0.2N hydrochloric acid to each well and cAMP-accumulation was measured by radioimmunoassay (RIA) using a commercially available kit (Amersham).

Experimental Groups

All test compounds were evaluated in a dose-response paradigm ranging from about 0.01 to about 30 µM. Controls and test compounds were evaluated in quadruplicate in a 96-well format. Cells were treated with vehicle, hFSH at $EC_{20}$ (1.85 ng/mL=53 pM), or the compounds in the presence or absence of hFSH at its $EC_{20}$ dose. The ability of the compounds to inhibit the cAMP-accumulation induced by hFSH was evaluated by RIA.

In every assay the $EC_{20}$ concentration was calculated and only those experiments in which the $EC_{20}$ concentrations were equal to 1.85±0.4 ng/mL were accepted as valid. In the 96-well format, the first column contained the negative control (assay media+0.1% DMSO), the second column contained the positive control, hFSH at its $EC_{20}$+0.1% DMSO (1.85 ng/ml or 53 pM), followed by six concentrations of the compound ranging from about 0.03-30 µM in the presence of the hFSH at its $EC_{20}$ concentration (1.85 ng/ml or 53 pM).

Along with the test compounds, FSH was also run as a positive control in the agonist mode using concentrations ranging from about 0.1-1000 ng/ml.

Selectivity Studies cAMP accumulation assays using CHO-25 (hTSH-R) cells were performed as described above for the CHO-3D2 cells with the following exceptions: CHO-25 cells were plated at a density of 50,000 cells/well (2). All test compounds were evaluated in a dose-response paradigm ranging from about 0.01 to 30 µM. Controls and test compounds were evaluated in quadruplicate. Cells were treated with vehicle, hTSH at $EC_{20}$ (5 nM; hTSH>98% pure, Cortex Biochem, Inc.), or the compounds in the presence or absence of the hTSH at its $EC_{20}$ concentration. The ability of the compounds to inhibit cAMP-accumulation induced by hTSH was evaluated by RIA.

Along with the test compounds, hTSH was also run as a positive control in the agonist mode using concentrations ranging from about 0.01 µM-1000 µM.

Non-Receptor Mediated Responses:

cAMP-accumulation assays using CHO-K1 (parental cell line) cells were performed as described above for the CHO-3D2 cells. All test compounds were evaluated in a dose-response paradigm ranging from about 0.01 to 30 µM. Controls and test compounds were evaluated in quadruplicate. Cells were treated with vehicle, 5 µM forskolin that induces the equivalent fmol/ml concentration of cAMP-accumulation induced by the hFSH at its $EC_{20}$ (5 µM forskolin, Sigma Chemical Co; previously calculated during characterization of the bio-assays), or the compounds in the presence or absence of the 5 µM forskolin. The ability of the compounds to inhibit the cAMP-accumulation induced by forskolin was evaluated by RIA.

Along with the test compounds, forskolin was also run as a positive control in agonist mode using concentrations ranging from about 0.01 µM to 1000 µM.

Analysis of Results cAMP accumulation is expressed as fmol/ml. cAMP accumulation in the agonist mode, or the ability of the compound to inhibit hFSH-, hTSH-, or forskolin-induced cAMP-accumulation in the antagonist mode, was compared to the appropriate negative and positive controls. Data were analyzed by one-way analysis of variance and significant differences between treatments and control determined by Least Significant Difference test.

Reference Compounds

Test compounds were compared to the effect of purified human FSH. In the paradigm, hFSH induced a concentration-dependent increase in cAMP accumulation, with apparent $EC_{80}$=22.55 ng/ml, $EC_{50}$=6.03 ng/ml and $EC_{20}$=1.85 ng/ml, calculated using a four-parameter logistic equation. The same comparison was performed with hTSH and forskolin.

Biological Activity

Based on the results obtained in the standard pharmacological test procedures, the compounds of this invention were shown to block cellular function of FSH, in vitro, including the production of second messenger cAMP and estradiol in rat ovarian granulosa cells. Representative compounds of this invention were found to selectively interact with the FSH receptor, but do not antagonize binding of FSH to its receptor (Table 1).

As such, the compounds of this invention may be useful as female contraceptive agents.

TABLE 1

| Example | CRE | | cAMP | |
|---|---|---|---|---|
| | % inhibition (µM) | IC50 (µM) | IC50 (µM) | % Efficacy |
| 2 | | 42.61 | 1.2 | 79 |
| 4 | | >30 | | |
| 5 | | 10.18 | 0.6 | 96 |
| 6 | | 3.3 | 0.3 | 81 |
| 7 | 26(30) | | | |
| 8 | | >30 | | |
| 10 | | 30 | | |
| 11 | | 30 | | |
| 12 | | >30 | | |

EXAMPLES

Example 1

2,2,2-Trichloro-1-{10-[(2'-methoxy-1,1'-biphenyl-4-yl)carbonyl]-10,11-dihydro-5H-pyrrolo[2,1-c][1,4]benzodiazepin-3-yl}ethanone Trichloroacetyl chloride (2.63 mL, 23.6 mmol) was added dropwise over five minutes to a solution of (2'-methoxy-biphenyl-4-yl)-(5H,11H-pyrrolo[2,1-c][1,4]benzodiazepin-10-yl)-methanone (3.0 g, 7.60 mmol) and N,N-diisopropyl-ethyl amine (2.65 mL, 15.2 mmol) in dichloromethane (60 mL). The reaction was stirred under nitrogen at room temperature overnight and then quenched with water. The organic layer was washed with 0.1N hydrochloric acid and water, dried over anhydrous magnesium sulfate, filtered and concentrated to an oil. The oil was purified by flash chromatography over silica gel Merck-60 using a 0-5% gradient of ethyl acetate in dichloromethane to give the title compound (2.34 g) as a yellow foam.

MS [(+)ESI, m/z]: 539 [M+H]+

Anal. Calcd for $C_{28}H_{21}Cl_3N_2O_3 + 0.2\ C_4H_8O_2$: C, 62.05; H, 4.09; N, 5.03. Found: C, 62.28; H, 4.47; N, 4.86.

Example 2

10-[(2'-Methoxy-1,1'-biphenyl-4-yl)carbonyl]-N-[(1-methyl-1H-pyrrol-2-yl)methyl]-10,11-dihydro-5H-pyrrolo[2,1-c][1,4]benzodiazepine-3-carboxamide To a suspension of 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (1.175 g, 2.17 mmole) in acetonitrile (15 mL) was added (1-methyl-1H-pyrrol-2-yl)methylamine (0.263 g, 2.38 mmole) followed by dimethylsulfoxide (0.710 g, 9.06 mmole) and triethylamine (0.400 g, 4 mmole). The mixture was heated under nitrogen at 80° C. for 4 hours. The solvent was removed in vacuo, and the residue was flash chromatographed on silica Merck-60 using a gradient of 0-25% of ethyl acetate in dichloromethane, to provide a yellow foam that yields a solid (0.464 g) upon treatment with ethyl acetate and hexane, mp 148-150° C.

MS [(+)ESI) m/z]: 531.16 [M+H]+

Anal. Calcd for $C_{33}H_{30}N_4O_3$: C, 74.70; H, 5.70; N, 10.56. Found: C, 74.56; H, 6.15; N, 10.20.

Example 3

2,2,2-Trichloro-1-{10-[(2,2',6'-trimethyl-1,1'-biphenyl-4-yl)carbonyl]-10,11-dihydro-5H-pyrrolo[2,1-c][1,4]benzodiazepin-3-yl}ethanone

Step A. 2,2',6'-Trimethyl-biphenyl-4-carboxylic acid methyl ester 2,6-Dimethyl boronic acid (13.7 g, 91 mmol) and 3-methyl benzoic acid methyl ester (20.9 g, 91 mmol) were dissolved in toluene (425 mL). Then ethanol (250 mL) and water (250 mL) were added followed by sodium carbonate (38.7 g, 365 mmole). The system was purged with nitrogen and then tetrakis triphenylphospine palladium (0) catalyst (10.5 g, 9 mmol) was added. The mixture was heated under nitrogen for 21 hours and filtered through celite. The cake was washed with a large amount of ethyl acetate, the combined filtrate was washed with water and brine, dried over anhydrous magnesium sulfate, and concentrated to give a solid. Flash chromatography of the residue over silica gel Merck-60 using a gradient of 0-20% ethyl acetate in hexane as the eluant, gave the title compound as a white solid (19.2 g, 83%).

Anal. Calcd. for $C_{17}H_{18}O_2$: C, 80.28; H, 7.13. Found: C, 80.37; H, 7.21.

Step B. 2,2',6'-Trimethyl-biphenyl-4-carboxylic acid

A solution of 2,2',6'-trimethyl-biphenyl-4-carboxylic acid methyl ester of Step A (18.5 g, 75.4 mmole) in tetrahydrofuran was treated with 1 N sodium hydroxide (250 mL) and heated at 90° C. for 20 hours. The mixture was acidified to pH ~1 with concentrated hydrochloric acid, extracted with dichloromethane, dried over anhydrous magnesium sulfate, and concentrated to give the title compound as a white powder (15.63 g). Recrystallization from aqueous ethanol provided white plates, m.p. 172-173° C.

MS [(−)ES, m/z]: 239.1 [M−H]−

Anal. Calcd. For. $C_{16}H_{16}O_2$: C, 79.97; H, 6.71. Found: C, 79.71; H, 6.70.

Step C. (5H,10)-[(2,2',6'-Trimethyl-1,1'-biphenyl-4-yl)carbonyl]-10,11-dihydro-5H-pyrrolo[2,1-c][1,4]benzodiazepine The 2,2',6'-trimethyl-biphenyl-4-carboxylic acid of Step B (11.4 g, 47.4 mmol) was stirred with 35 mL (479 mmol) of thionyl chloride, and heated to 70° C. for 3 hours. The excess thionyl chloride was removed under vacuum with the aid of toluene. The crude acid chloride was dissolved in dichloromethane (100 mL) and a solution of 10,11-dihydro-5H-pyrrolo[2,1-c][1,4]benzodiazepine (12.23 g, 47.4 mmol) in dichloromethane (50 mL) was added dropwise. After stirring overnight at room temperature, the mixture was washed with water, 1N hydrochloric acid, saturated aqueous sodium bicarbonate, and brine, dried over anhydrous magnesium sulfate, filtered and concentrated. Flash chromatography of the residue on silica gel Marck-60 using a gradient from 1:1 to 4:1 of dichloromethane in hexane gave the pure title compound which was recrystallized from aqueous ethanol as fine translucent plates, m.p. 170-171° C.

MS [(+)ES, m/]: 407.2 [M+H]+

Anal. Calcd for $C_{28}H_{26}N_2O \cdot 0.15\ H_2O$: C, 82.18; H, 6.48; N, 6.85. Found: C, 82.28; H, 6.32; N, 6.76.

Step D. 2,2,2-Trichloro-1-{10-[(2,2',6'-trimethyl-1,1'-biphenyl-4-yl)carbonyl]-10,11-dihydro-5H-pyrrolo[2,1-c][1,4]benzodiazepin-3-yl}ethanone 0.15 water To a solution of (5H,10)-[(2,2',6'-trimethyl-1,1'-biphenyl-4-yl)carbonyl]-10,11-dihydro-5H-pyrrolo[2,1-c][1,4]benzodiazepine of Step C (7.934 g, 19.5 mmol) in dichloromethane (160 mL) was added trichloroacetyl chloride (11 g, 60.5 mmol, 3.1 eq.), N,N-diisopropylethyl amine (5.54 g, 43 mmol, 2.2 eq.) and 4-(dimethylamino)pyridine (10 mole %). The mixture was stirred for 16.5 hours at room temperature, then quenched with water (100 mL) and stirred for 1 hour. The organic layer was washed with 0.1N hydrochloric acid and brine, dried over anhydrous magnesium sulfate, and concentrated to a yellow foam.

MS [(+)ES, m/z]: 551.1 [M+H]+

Anal. Calcd. For. $C_{30}H_{25}Cl_3N_2O_2 \cdot H_2O$: C, 64.97; N, 4.60; H, 5.05. Found: C, 64.79; H, 4.97; H, 4.58.

Example 4

N-[(5-Methylisoxazol-3-yl)methyl]-10-[(2,2',6'-trimethyl-1,1'-biphenyl-4-yl)carbonyl]-10,11-dihydro-5H-pyrrolo[2,1-c][1,4]benzodiazepine-3-carboxamide The title compound was prepared according to the procedure of Example 2 starting from 2,2,2-trichloro-1-{10-[(2,2',6'-trimethyl-1,1'-biphenyl-4-yl)carbonyl]-10,11-dihydro-5H-pyrrolo[2,1-c][1,4]benzodiazepin-3-yl}ethanone of Example 3 (1.8 g, 3.26 mmole), (5-methyl-3-isoxazolyl)methylamine (0.305 g, 2.7 mmole), dimethylsulfoxide (1.06 g, 13.6 mmole), and triethylamine (0.605 g, 6 mmole) in 20 mL of acetonitrile. The residue was flash chromatographed on silica Merck-60 using a gradient from 0 to 35% of ethyl acetate in dichloromethane, to provide an orange-yellow foam. Recrystallization from ethyl acetate/dichloromethane/hexane gave a white powder (0.334 g), m.p. 233-234° C.

MS [(+)ESI, m/z]: 545.2 [M+H]+

Anal. Calcd. for $C_{34}H_{32}N_4O_3 \cdot 0.15\ C_5H_{10}O_2$: C, 74.49; H, 6.00; N, 10.04. Found: C, 74.46; H, 6.11; N, 10.06.

53

Example 5

10-[(2'-Methoxy-1,1'-biphenyl-4-yl)carbonyl]-N-[(5-methylisoxazol-3-yl)methyl]-10,11-dihydro-5H-pyrrolo[2,1-c][1,4]benzodiazepine-3-carboxamide The title compound was prepared according to the procedure of Example 2 starting from 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (1.483 g, 2.75 mmole), (5-methyl-3-isoxazoyl)methylamine (0.256 g 1.0 eq), dimethylsulfoxide (5.0 eq, 0.896 g, 11.45 mmole), and triethylamine (2.2 eq, 0.510 g, 5 mmole) in 20 mL of acetonitrile. The residue was absorbed on silica gel Merck-60 and flash chromatographed using a gradient from 0 to 20% of ethyl acetate in dichloromethane, to provide a foam (0.460 g) which yielded an off-white solid upon treatment with ethyl acetate/hexane, m.p. 111-113° C.

MS [+)ESI, m/z]: 533.12 [M+H]$^+$

Anal. Calcd for $C_{32}H_{28}N_4O_4$: C, 72.17; H, 5.30; N, 10.52. Found: C, 71.85; H, 5.27; N, 10.25.

Example 6

N-[(2,5-Dimethyl-3-furyl)methyl]-10-[(2'-methoxy-1,1'-biphenyl-4-yl)carbonyl]-10,11-dihydro-5H-pyrrolo[2,1-c][1,4]benzodiazepine-3-carboxamide The title compound was prepared according to the procedure of Example 2 starting from 2,5-dimethyl-3-furyl)methylamine (0.264 g, 2.1 mmole), 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (1.138 g, 2.1 mmole), triethylamine (0.470 g, 2.2 eq., 4.6 mmole) and dimethylsulfoxide (1.1 g, 5.0 eq., 10.5 mmole) in 20 mL of acetonitrile. Flash chromatography of the residue on silica Merck-60 using a gradient elution of 30 to 45% ethyl acetate in hexane gave a white powder (0.453 g). Further purification was achieved by prep HPLC, Primesphere C18, 2×25 cm column, 68% acetonitrile in water containing trifluoroacetic acid, 100 ml/min, 254 nm detection. The pure fractions were neutralized with ammonium hydroxide and evaporated to an amorphous solid (0.153 g).

MS [(+)ESI, m/z]: 546.2 [M+H]$^+$
MS [(−)ESI, m/z]: 544.2 [M−H]$^-$

Example 7

N-[(4-Benzylmorpholin-2-yl)methyl]-10-[(2'-methoxy-1,1'-biphenyl-4-yl)carbonyl]-10,11-dihydro-5H-pyrrolo[2,1-c][1,4]benzodiazepine-3-carboxamide The title compound was prepared according to the procedure of Example 2 starting from 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone of Example 1 (0.619 g, 1.15 mmole), (4-benzyl-1,4-oxazinan-2-yl)-methylamine (01.97 g, 0.955 mmole), dimethylsulfoxide (0.374 g, 4.8 mmole), and triethylamine (0.213 g, 2.1 mmole) in 15 mL of acetonitrile. The residue was adsorbed on silica Merck-60 and purified by flash chromatography (0-75% ethyl acetate in dichloromethane) to provide an off white solid (0.241 g), m.p. 180-182° C.

MS [(+)ESI, m/z]: 627.19 [M+H]$^+$

Anal. Calcd for $C_{39}H_{38}N_4O_4$: 0.35 $C_5H_{10}O_2$: C, 73.79; H, 6.25; N, 8.52. Found: C, 73.62; H, 6.07; N, 8.55.

Example 8

N-[(1-Methyl-1H-pyrrol-2-yl)methyl]-10-[(2,2',6'-trimethyl-1,1'-biphenyl-4-yl)carbonyl]-10,11-dihydro-5H-pyrrolo[2,1-c][1,4]benzodiazepine-3-carboxamide The title compound was prepared according to procedure of Example 2 starting from 2,2,2-trichloro-1-{10-[(2,2',6'-trimethyl-1,1'-biphenyl-4-yl)carbonyl]-10,11-dihydro-5H-pyrrolo[2,1-c][1,4]benzodiazepin-3-yl}ethanone of Example 3 (1.4 g, 2.5 mmole), (1-methyl-1H-pyrrol-2-yl)methylamine (0.234 g, 2.1 mmole), dimethylsulfoxide (0.822 g, 10.5 mmole) and triethyl amine (0.470 g, 4.6 mmole) in 15 mL of acetonitrile, Flash chromatography of the residue on silica gel Merck-60 (0-25% ethyl acetate in dichloromethane) gave a foam (0.924 g) which solidified upon treatment with ethyl acetate/hexane/dichloromethane, mp. 222-224° C.

MS [(+)ESI, m/z]: 543.3 [M+H]$^+$; [(−)ESI, m/z]: 541.3 [M−H]$^-$

Example 9

2,2,2-Trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone

Step A. Methyl 2,2'-dimethyl-1,1'-biphenyl-4-carboxylate

A mixture of methyl 4-bromo-3-methylbenzoate (25.0 g, 110 mmol), o-tolylboronic acid (16.5 g, 120 mmol) and potassium carbonate (50 g, 360 mmol) in dioxane:water (300 mL:200 mL) was purged with nitrogen for 1 hour. [1,1'-bis(Diphenylphosphino)ferrocene]dichloropalladium [II] (4.5 g, 5.5 mmol) was added and the reaction mixture heated to 100° C. with vigorous stirring for 3.5 hours. The cooled reaction mixture was filtered through Celite and the cake washed with ethyl acetate (500 mL). The combined organic phases were washed with 1 M aqueous sodium hydroxide (500 mL) and brine (500 mL), dried over anhydrous potassium carbonate, filtered and concentrated in vacuo to afford a dark oil (28.6 g). Purification by flash chromatography using 2% ethyl acetate in hexanes as solvent provided the title compound (24.7 g) as a pale yellow oil.

HRMS. Calcd for $C_{16}H_{17}O_2$: 241.12231. Found [(+)ESI, m/z]: 241.12205.

Anal. Calcd for $C_{16}H_{16}O_2$: C, 79.97; H, 6.71. Found: C, 79.67; H, 6.61.

Step B. 2,2'-Dimethyl-biphenyl-4-carboxylic acid

To a solution of methyl 2,2'-dimethyl-1,1'-biphenyl-4-carboxylate of Step A (24.7 g, 103 mmol) in 5:1 tetrahydrofuran:methanol (200 mL) was added 1 M aqueous sodium hydroxide (108 mL, 108 mmol). The reaction mixture heated at reflux for 1 hour, cooled and then concentrated in vacuo to remove organic solvents. The resulting aqueous solution was cooled to 0° C. and 2 M aqueous hydrochloric acid (60 mL, 120 mmol) added slowly followed by water (60 mL) to facilitate stirring of the precipitated product. The suspension was stirred for 1 h at 0° C. then filtered to afford the title compound (22.6 g) as a white solid, m. p. 140-143° C.

MS [(+)ESI, m/z]: 225 [M−H]$^-$.

Step C. (10,11-Dihydro-5H-pyrrolo[2,1-c][1,4]benzodiazepin-10-yl)-(2,2'-dimethyl-biphenyl-4-yl)-methanone To a suspension of 2,2'-dimethyl-biphenyl-4-carboxylic acid of Step B (22.4 g, 99.0 mmol) in dry dichloromethane (500 mL) at room temperature under nitrogen was added dry N,N-dimethylformamide (5 mL) followed by the dropwise addition of 2.0 M solution of oxalyl chloride in dichloromethane (60 mL, 120 mmol). The reaction mixture was stirred at room temperature for 2 hours then concentrated in vacuo and the residue redissolved in dry dichloromethane (200 mL). The solution was concentrated in vacuo to afford the crude acid chloride as a brown oil. The acid chloride was dissolved in dichloromethane (500 mL), 10,11-dihydro-5H-pyrrolo[2,1-c][1,4]benzodiazepine (21.9 g, 119 mmol) was added followed by N,N-diisopropylethylamine (87 mL, 500 mmol) and the reaction mixture stirred at room temperature under nitrogen for 16 hours. The reaction mixture was then washed with 1 M aqueous hydrochloric acid (5×1 L), 10% aqueous sodium hydroxide (1 L) and brine (500 mL), dried over anhydrous magnesium sulfate, filtered and concentrated in vacuo to give a dark foam. Purification by flash chromatography using a solvent gradient of 2.5 to 40% ethyl acetate in hexane gave a tan solid that was recrystallized from ethyl acetate/hexane to afford the title compound (12.4 g) as a pale orange solid. Purification of the mother liquors by flash chromatography yielded additional title compound (11.5 g) as a white solid, m.p. 145-148° C.

MS [(+)ESI, m/z]: 393 [M+H]$^+$.

Anal. Calcd for $C_{27}H_{24}N_2O$: C, 82.62; H, 6.16; N, 7.14. Found: C, 82.26; H, 5.83; N, 6.50.

Step D. 2,2,2-Trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone To a solution of (10,11-dihydro-5H-pyrrolo[2,1-c][1,4]benzodiazepine-10-yl)-(2,2'-dimethyl-biphenyl-4-yl)-methanone of Step C (8.38 mmol) and triethylamine (16.76 mmol) in dichloromethane (30 mL) at −5° C. was added, rapidly dropwise, trichloroacetyl chloride (25 mmol). The mixture was allowed to stir and warm to room temperature overnight. The mixture was washed with 0.1N hydrochloric acid and dilute brine, then dried over anhydrous sodium sulfate, and evaporated to leave a light green oil. The compound was purified by filtration over a plug of Merck silica gel-60 eluting with dichloromethane and then treated with hot ethyl acetate/hexane (3/1) to yield a light yellow crystalline solid, m.p. 212-214° C.

MS [(+)(ESI, m/z]: 537 [M+H]$^+$

Anal. Calcd for $C_{29}H_{23}Cl_3N_2O_2$: C, 64.76; H, 4.31; N, 5.21. Found: C, 64.70; H, 4.35; N, 4.96.

Example 10

10-[(2,2'-Dimethyl-1,1'-biphenyl-4-yl)carbonyl]-N-{[5-(4-methoxyphenyl)-1,2,4-oxadiazol-3-yl]methyl}-10,11-dihydro-5H-pyrrolo[2,1-c][1,4]benzodiazepine-3-carboxamide

Step A. [5-(4-Methoxyphenyl)-1,2,4-oxadiazol-3-yl]methylamine

To a solution of 3-chloromethyl-5-(4-methoxy-phenyl)-[1,2,4]oxadiazole (8.90 mmol) in N,N-dimethylformamide (10 mL) was added sodium azide (17.8 mmol). This mixture was stirred at room temperature for 20 hours. The reaction mixture was poured into water (30 mL) and extracted with dichloromethane (3×). The combined organic extracts were combined and washed with water (2×), dried over anhydrous sodium sulfate, and evaporated. Then clear oily residue was placed under high vacuum and gently warmed for 18 hours. Upon cooling the material solidified. This solid was dissolved in tetrahydrofuran (15 mL) and treated with triphenylphosphine (9.0 mmol). Bubbling was immediately evident. This mixture was stirred for 16 hours and then treated with water (3.0 mL). This was heated in a 45° C. oil bath for 3 hours. The product was purified by flash chromatography (silica gel; 2:1 ether/dichloromethane), m.p. 66-68° C.

MS [(+)(ESI, m/z]: 206 [M+H]$^+$

Anal. Calcd for $C_{10}H_{11}N_3O_2$: C, 58.53; H, 5.40; N, 20.48. Found: C, 58.5; H, 5.38; N, 20.59.

Step B. 10-[(2,2'-Dimethyl-1,1'-biphenyl-4-yl)carbonyl]-N-{[5-(4-methoxyphenyl)-1,2,4-oxadiazol-3-yl]methyl}-10,11-dihydro-5H-pyrrolo[2,1-c][1,4]benzodiazepine-3-carboxamide A mixture of 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 9 (0.26 mmol), dimethylsulfoxide (100 uL) and [5-(4-methoxyphenyl)-1,2,4-oxadiazol-3-yl]methylamine of Step A (0.546 mmol) in acetonitrile (2.5 mL) was heated to 85° C. for 16 hours. After cooling the solvent was evaporated and the residue was taken up in dichloromethane (10 mL). This was washed with water (2×), dried over anhydrous sodium sulfate, and evaporated. The residue was purified by HPLC (Normal phase, Luna CN bonded packing) and crystallized from ethyl acetate/hexane, m.p. 133-135° C.

MS [(+) ESI, m/z]: 622 [M+H]$^+$

Anal. Calcd for $C_{38}H_{33}N_5O_4$: C, 73.18; H, 5.33; N, 11.23. Found: C, 71.95; H, 5.64; N, 11.52.

Example 11

N-{[2-(4-Chlorophenyl)-1,3-thiazol-4-yl]methyl}-10-[(2,2'-dimethyl-1,1'-biphenyl-4-yl)carbonyl]-10,11-dihydro-5H-pyrrolo[2,1-c][1,4]benzodiazepine-3-carboxamide

Step A. 2-(4-Chlorophenyl)-1,3-thiazol-4-yl]methylamine

The title compound was prepared from 4-chloromethyl-2-(4-chloro-phenyl)-thiazole according to the procedure of Example 10, Step A, m.p. 61-64° C.

MS [(+)ESI, m/z]: 225 [M+H]$^+$

Anal. Calcd for $C_{10}H_9ClN_2S$: C, 53.45; H, 4.04; N, 12.47. Found: C, 53.57; H, 4.05; N, 12.45.

Step B. N-{[2-(4-Chlorophenyl)-1,3-thiazol-4-yl]methyl}-10-[(2,2'-dimethyl-1,1'-biphenyl-4-yl)carbonyl]-10,11-dihydro-5H-pyrrolo[2,1-c][1,4]benzodiazepine-3-carboxamide The title compound was synthesized from 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3- yl}ethanone of Example 9 and 2-(4-chloro-phenyl)-thiazol-4-yl]-methylamine of Step A according to the procedure of Example 10, Step B, m.p. 198-201° C.

MS [(+)ESI, m/z]: 641 [M+H]+

Example 12

10-[(2,2'-Dimethyl-1,1'-biphenyl-4-yl)carbonyl]-N-(piperidin-3-ylmethyl)-10,11-dihydro-5H-pyrrolo[2,1-c][1,4]benzodiazepine-3-carboxamide Step A. tert-Butyl 3-{[({10-[(2,2'-dimethyl-1,1'-biphenyl-4-yl)carbonyl]-10,1dihydro-5H-pyrrolo[2,1-c][1,4]benzodiazepin-3-yl}carbonyl)amino]methyl}piperidine-1-carboxylate To a suspension of 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Example 9 (0.54 g, 1.0 mmol) and 3-aminomethyl-piperidine-1-carboxylic acid tert-butyl ester (0.43 g, 2.0 mmol) in dry acetonitrile (5 mL) was added dimethylsulfoxide (0.35 mL, 4.9 mmol) and the reaction mixture heated to 80° C. under nitrogen for 3 days. The cooled reaction mixture was diluted with dichloromethane (25 mL), washed with water (2×25 mL) and brine (25 mL), dried over anhydrous potassium carbonate, filtered and concentrated in vacuo to afford a brown oil (0.81 g). Purification by flash chromatography using a solvent gradient of 3 to 20% ethyl acetate in dichloromethane gave the title compound (0.45 g) as a white foam.

HRMS. Calcd for $C_{39}H_{45}N_4O_4$: 633.34354. Found [(+) ESI, m/z]: 633.34262.

Step B. 10-[(2,2'-Dimethyl-1,1'-biphenyl-4-yl)carbonyl]-N-(piperidin-3-ylmethyl)-10,11-dihydro-5H-pyrrolo[2,1-c][1,4]benzodiazepine-3-carboxamide To a solution of tert-butyl 3-{[({10-[(2,2'-dimethyl-1,1'-biphenyl-4-yl)carbonyl]-10,11-dihydro-5H-pyrrolo[2,1-c][1,4]benzodiazepin-3-yl}carbonyl)amino]methyl}piperidine-1-carboxylate of Step A (0.42 g, 0.66 mmol) in dry dichloromethane (3 mL) was added trifluoroacetic acid (0.51 mL, 6.6 mmol) and the reaction mixture stirred at room temperature under nitrogen for 20 hours. The reaction mixture was then diluted with dichloromethane (50 mL), washed with 1 M sodium hydroxide solution (50 mL) and brine (50 mL), dried over anhydrous magnesium sulfate, filtered and concentrated in vacuo to afford a pink glass. Purification by flash chromatography using a solvent gradient of 2.5 to 10% ammonia saturated methanol in dichloromethane gave a pale yellow oil (0.31 g). Crystallization from diethyl ether (2 mL) afforded the title compound (0.19 g) as a pale yellow solid.

HRMS. Calcd for $C_{34}H_{37}N_4O_2$: 533.29111. Found [(+) ESI, m/z]: 533.29102.

All references, including but not limited to articles, texts, patents, patent applications, and books, cited herein are hereby incorporated by reference in their entirety.

What is claimed is:

1. A compound represented by the Formula I:

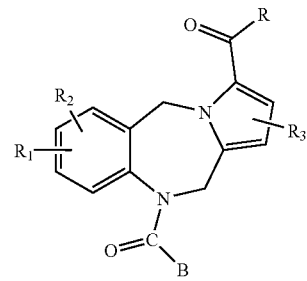

or a pharmaceutically acceptable salt thereof,
wherein
$R_1$ and $R_2$ are independently selected from hydrogen, ($C_1$-$C_6$)alkyl, halogen, cyano, trifluoromethyl, hydroxyl, ($C_1$-$C_6$)alkoxy, —$OCF_3$, carboxy, ($C_1$-$C_6$ alkoxy)carbonyl, —$CONH_2$, —CONH[($C_1$-$C_6$)alkyl], —CON[($C_1$-$C_6$)alkyl]$_2$, amino, ($C_1$-$C_6$)alkylamino or —NHCO[($C_1$-$C_6$)alkyl];

$R_3$ is a substituent selected from hydrogen, ($C_1$-$C_6$)alkyl, ($C_1$-$C_6$)alkoxy, hydroxy, amino, ($C_1$-$C_6$)alkylamino, —C(O)($C_1$-$C_6$)alkyl, or halogen;

B is

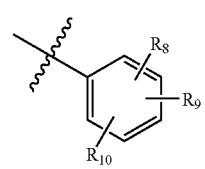

where Q is

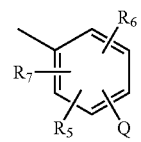 (a)

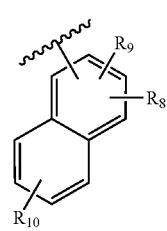 (b)

wherein $R_5$, $R_6$, $R_7$, $R_8$, $R_9$ and $R_{10}$ are independently, selected from the group consisting of hydrogen, alkyl, alkoxy, hydroxyalkyl, alkyloxyalkyl, ($C_2$-$C_7$)acyloxy ($C_1$-$C_6$)alkyl, ($C_1$-$C_6$alkyl)carbonyl, ($C_2$-$C_6$)alkenyl, ($C_2$-$C_6$)alkynyl, ($C_3$-$C_8$)cycloalkyl, formyl, ($C_3$-$C_8$) cycloalkylcarbonyl, carboxy, ($C_1$-$C_6$)alkoxycarbonyl, ($C_3$-$C_8$cycloalkyl)oxycarbonyl, aryl($C_1$-$C_6$)alkyloxycarbonyl, carbamoyl, —O—$CH_2$—CH=$CH_2$, ($C_1$-$C_6$)alkyl substituted with 1-3 halogen atoms, halogen, $OCF_3$, thioalkyl, —C(O)alkyl, —C(O)aryl optionally substituted by alkyl; hydroxy, —CH(OH)alkyl, —CH(alkoxy)alkyl, nitro, —SO$_2$alkyl, aminosulfonyl, (C$_1$-C$_6$)alkylaminosulfonyl, —SO$_2$NHR$_{11}$, —SO$_2$N(R$_{11}$)$_2$, —OC(O)N[(C$_1$-C$_6$)alkyl]$_2$, —CONH[(C$_1$-C$_6$)alkyl], —CON[(C$_1$-C$_6$)alkyl]$_2$, —(CH$_2$)$_p$CN, (C$_1$-C$_6$)alkylamino, di-(C$_1$-C$_6$)alkylamino, (C$_1$-C$_6$)alkyl di-(C$_1$-C$_6$)alkylamino, —(CH$_2$)$_p$ NR$_{13}$R$_{14}$, —(CH$_2$)$_p$CONR$_{13}$R$_{14}$, —(CH$_2$)$_p$ COOR$_{12}$, —CH=NOH, —CH=NO—(C$_1$-C$_6$)alkyl, trifluoromethylthio,

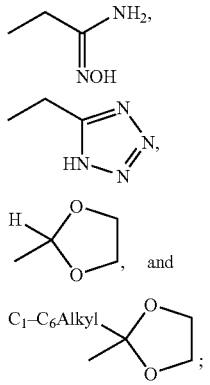

R$_{11}$ and R$_{12}$ are hydrogen, C$_3$-C$_8$ cycloalkyl, or (C$_1$-C$_6$)alkyl;

R$_{13}$ and R$_{14}$ are hydrogen, C$_3$-C$_8$ cycloalkyl, or (C$_1$-C$_6$)alkyl, or R$_{13}$ and R$_{14}$ can be taken together with the nitrogen to which they are attached to form a 4-6 membered saturated ring optionally containing O, S or N;

p is 0 or 1;

R is the moiety

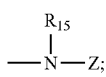

R$_{15}$ is hydrogen or (C$_1$-C$_6$)alkyl;

Z has the formula —L—M;

L has the formula

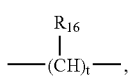

wherein t is an integer from 1 to 2;

R$_{16}$ is hydrogen or (C$_1$-C$_6$)alkyl,

M is selected from the group consisting of

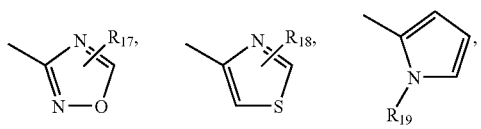

-continued

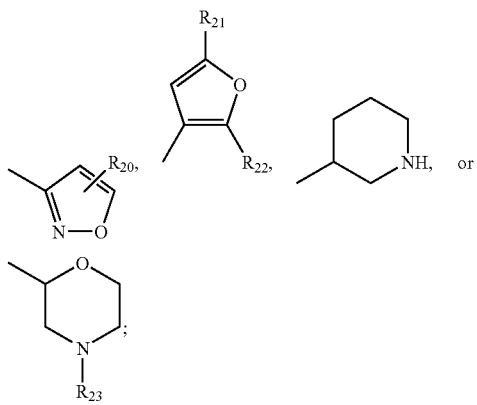

wherein R$_{17}$ and R$_{18}$ are each, independently, an optionally substituted aryl;

R$_{19}$, R$_{20}$, R$_{21}$ and R$_{22}$ are each, independently, (C$_1$-C$_6$)alkyl;

R$_{23}$ is alkyl, or an optionally substituted (C$_6$-C$_{20}$) aralkyl.

2. A compound according to claim 1, or pharmaceutically acceptable salt thereof, wherein R$_{15}$ and R$_{16}$ are each hydrogen; and t is 1.

3. A compound according to claim 2, wherein M is selected from the group consisting of:

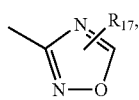

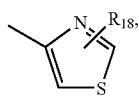

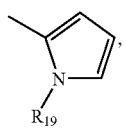

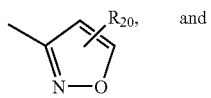

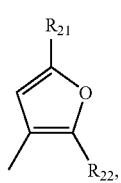

or pharmaceutically acceptable salt thereof.

4. A compound according to claim 2, wherein M is selected from the group consisting of

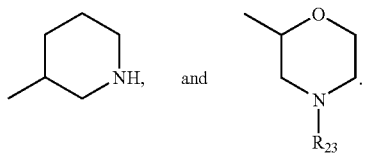

or pharmaceutically acceptable salt thereof.

5. A compound according to claim 2, wherein B has the formula:

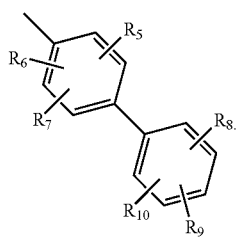

or pharmaceutically acceptable salt thereof.

6. A compound according to claim 2, wherein $R_1$, $R_2$ and $R_3$ are each hydrogen, or pharmaceutically acceptable salt thereof.

7. A compound according to claim 1, having the Formula:

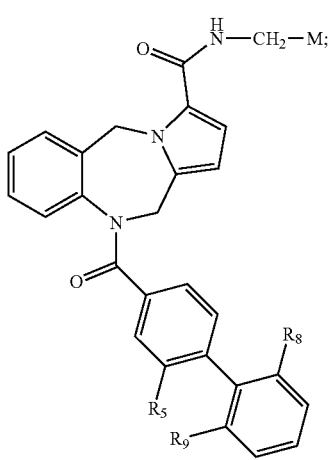

or a pharmaceutically acceptable salt thereof.

8. A compound according to claim 7, wherein:
$R_5$ is selected from H, and $C_1$-$C_3$ alkyl; and
$R_8$ and $R_9$ are independently selected from H, $C_1$-$C_3$ alkyl, and $C_1$-$C_3$ alkoxy;
or pharmaceutically acceptable salt thereof.

9. A compound according to claim 1, wherein M is

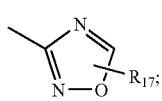

wherein $R_{17}$ is an optionally substituted aryl;
or pharmaceutically acceptable salt thereof.

10. A compound according to claim 8, wherein M is

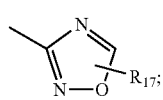

wherein $R_{17}$ is an optionally substituted aryl;
or pharmaceutically acceptable salt thereof.

11. A compound according to claim 1, having the following Formula:

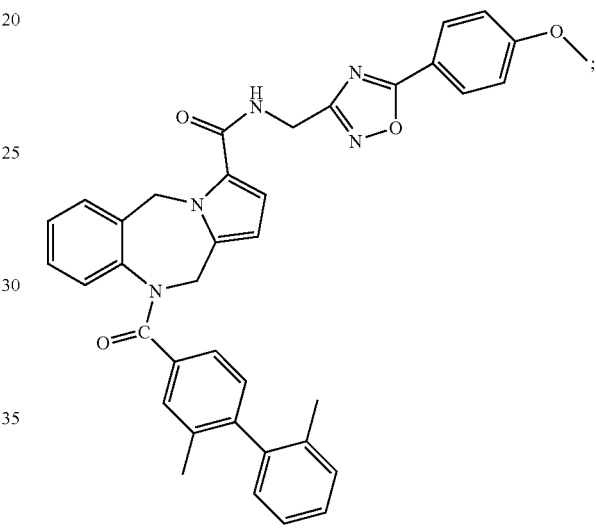

or pharmaceutically acceptable salt thereof.

12. A compound of claim 1 wherein in Formula I, M is

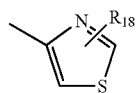

wherein $R_{18}$ is an optionally substituted aryl;
or a pharmaceutically acceptable salt thereof.

13. A compound of claim 8 wherein M is

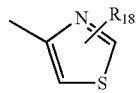

wherein $R_{18}$ is an optionally substituted aryl;
or a pharmaceutically acceptable salt thereof.

14. A compound according to claim 1, having the following formula:

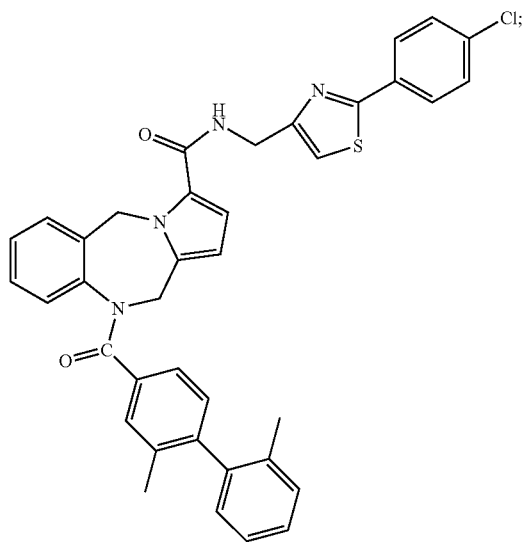

or pharmaceutically acceptable salt thereof.

15. A compound of claim 1 wherein M is

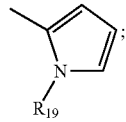

wherein $R_{19}$ is $C_1$-$C_6$ alkyl;
or a pharmaceutically acceptable salt thereof.

16. A compound according to claim 8 wherein M is

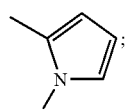

wherein $R_{19}$ is $C_1$-$C_6$ alkyl;
or a pharmaceutically acceptable salt thereof.

17. A compound according to claim 1, having the following formula:

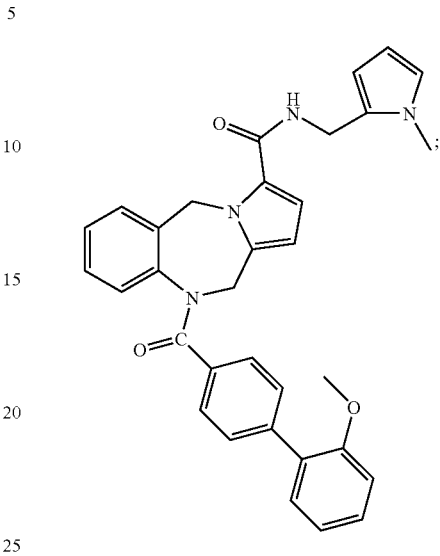

or pharmaceutically acceptable salt thereof.

18. A compound according to claim 1 having the following formula:

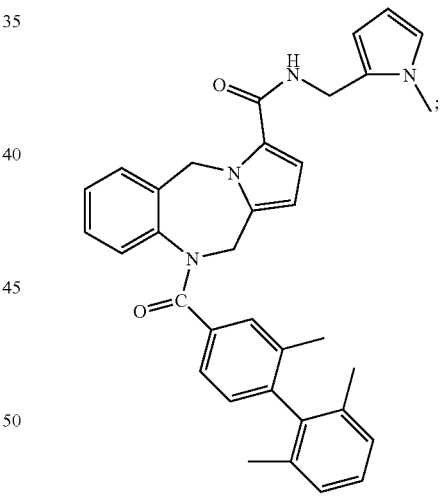

or pharmaceutically acceptable salt thereof.

19. A compound of claim 1 wherein M is

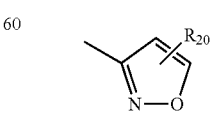

wherein $R_{20}$ is $C_1$-$C_6$ alkyl;
or a pharmaceutically acceptable salt thereof.

20. A compound according to claim 8 wherein M is

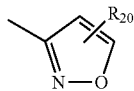

wherein R$_{20}$ is C$_1$-C$_6$alkyl;
or a pharmaceutically acceptable salt thereof.

21. A compound according to claim 1, having the following formula:

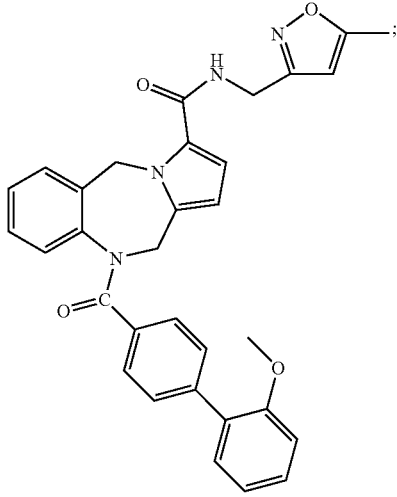

or pharmaceutically acceptable salt thereof.

22. A compound according to claim 1, having the following formula:

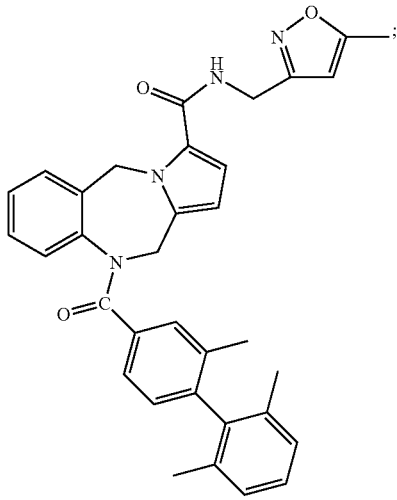

or pharmaceutically acceptable salt thereof.

23. A compound of claim 1 wherein M is

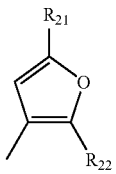

wherein R$_{21}$ and R$_{22}$ are each independently C$_1$-C$_6$ alkyl;
or pharmaceutically acceptable salt thereof.

24. A compound according to claim 8 wherein M is

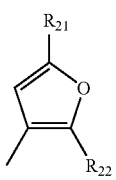

wherein R$_{21}$ and R$_{22}$ are each independently C$_1$-C$_6$ alkyl;
or pharmaceutically acceptable salt thereof.

25. A compound according to claim 1 having the following formula:

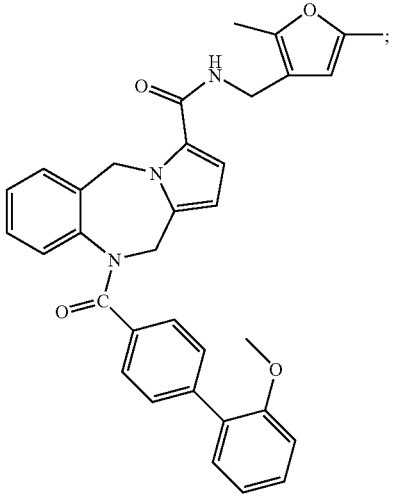

or pharmaceutically acceptable salt thereof.

26. A compound according to claim 1 wherein M is

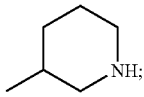

or pharmaceutically acceptable salt thereof.

27. A compound according to claim 8 wherein M is

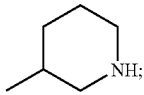

or pharmaceutically acceptable salt thereof.

28. A compound according to claim 1 having the following formula:

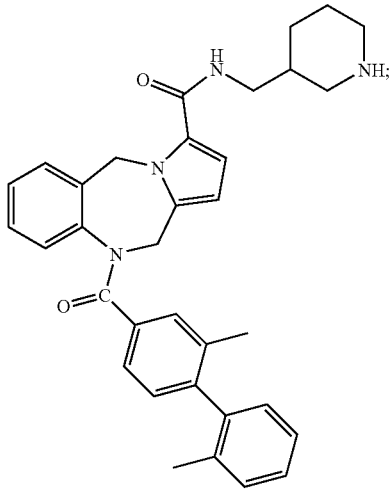

or pharmaceutically acceptable salt thereof.

29. A compound according to claim 1 wherein M is

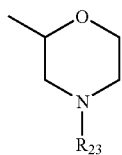

wherein $R_{23}$ is optionally substituted $C_7$-$C_{20}$ aralkyl; or pharmaceutically acceptable salt thereof.

30. A compound according to claim 8 wherein M is

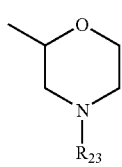

wherein $R_{23}$ is optionally substituted $C_7$-$C_{20}$ aralkyl; or pharmaceutically acceptable salt thereof.

31. A compound according to claim 1 having the following formula:

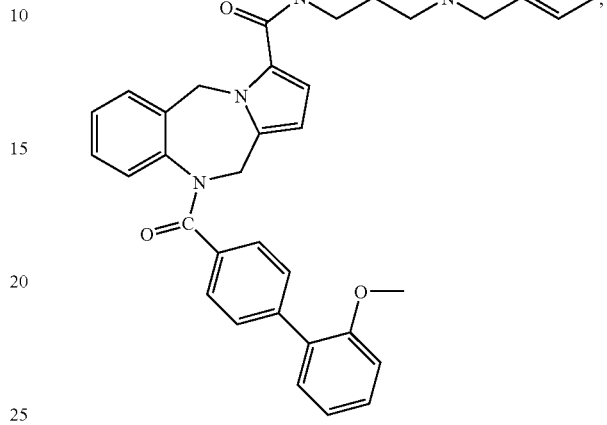

or pharmaceutically acceptable salt thereof.

32. A method for preparing a compound of claim 1, comprising:

reacting a trichloroacetyl compound of formula (2)

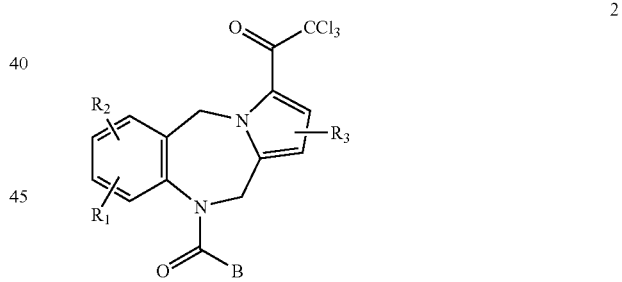

with an appropriately substituted primary or secondary amine of formula (3)

RH    (3)

under conditions sufficient to yield a compound of Formula (I).

33. The method of claim 32, wherein said reaction occurs in the presence of 1,4-dioxane, dimethylsulfoxide, or both.

34. The method of claim 33 wherein said reaction occurs in the presence of an organic base.

35. The method of claim 34 wherein said organic based is a tertiary amine selected from triethyl amine and N,N-diisopropylethylamine.

36. The method of claim 32, wherein said trichloroacetyl compound of formula (2) is prepared by:

reacting a tricyclic azepine of formula (1)

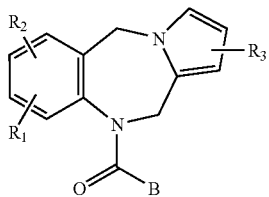

with perhaloalkanoyl halide under conditions sufficient to provide the desired trichloroacetyl compound of formula (2).

37. A method for making a compound of Formula I according to claim 1, comprising:
coupling a compound of Formula (4)

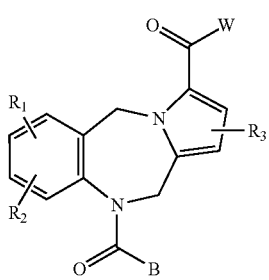

where W is OH or halogen;
with an appropriately substituted primary or secondary amine of formula (3)

RH  (3)

under conditions sufficient to yield a compound of formula (I) of claim 1.

38. The method of claim 37 wherein said coupling comprises:
reacting said carboxylic acid (4) with a primary or secondary amine of formula (3) in the presence of at least one of an activating reagent or a coupling reagent under conditions sufficient to yield a compound of formula (I).

39. The method of claim 38, wherein said coupling reagent is selected from hydroxybenzotriazole tetramethyluronium hexafluorophosphate, diphenylphosphoryl azide, diethyl cyano phosphonate, or benzotriazol-1-yl-oxy-tris-(dimethylamino)phosphonium hexafluorophosphate.

40. The method of claim 37 wherein said compound of Formula 4 wherein W is Cl or Br is prepared by conversion of a compound of Formula 4 wherein W is OH.

41. The method of claim 40, wherein said conversion comprises:
reacting said compound of Formula 4 wherein W is OH with thionyl halide or an oxalyl halide.

42. A method of preparing a compound of Formula I according to claim 1, comprising:
reacting a tricyclic diazepine of formula (1)

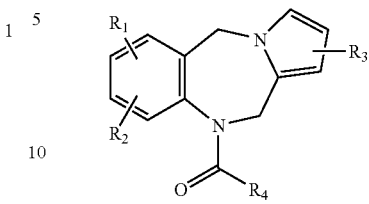

with diphosgene and a primary or secondary amine of formula (3)

RH  (3)

in an aprotic solvent under conditions sufficient to yield a compound according to formula (I).

43. A method for preparing a compound of claim 1, comprising:
reacting a trichloroacetyl compound of formula (26)

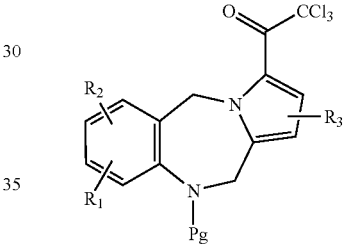

where Pg is a protecting group, with an appropriately substituted primary or secondary amine of formula (3)

RH  (3)

under conditions sufficient to yield an intermediate amide of formula (27)

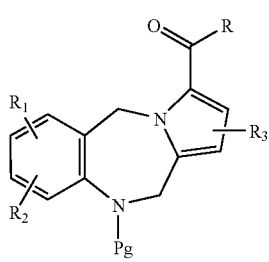

44. The method of claim 43, wherein Pg is selected from the group consisting of a fluorenyl alkoxy carbonyl and an alkoxy carbonyl.

45. The method of claim 43, further comprising deprotecting the intermediate amide of formula (27) under conditions sufficient to yield an intermediate of formula (28)

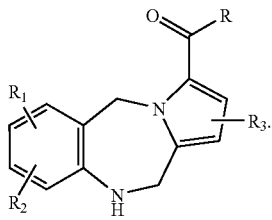

(28)

46. The method of claim 43, wherein said trichloroacetyl compound of formula (26) is prepared by:

reacting a tricyclic azepine of formula (1)

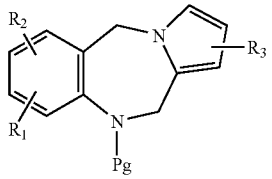

(1)

where Pg is a protecting group, with perhaloalkanoyl halide under conditions sufficient to provide the desired trichloroacetyl compound of formula (26).

47. A method for preparing a compound according to claim 1, comprising:

reacting a compound of formula (26)

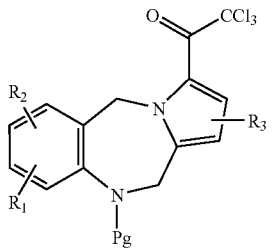

(26)

where Pg is a protecting group, with an aqueous base, and removing Pg to yield an intermediate of formula (29)

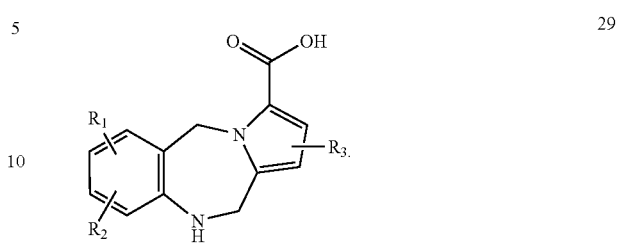

(29)

48. The method of claim 47, further comprising treating the intermediate of formula (29) with an activating agent and an appropriately substituted primary or secondary amine of formula (3)

RH    (3)

under conditions sufficient to yield an intermediate of formula (28)

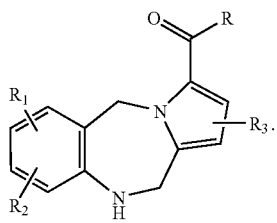

(28)

49. The method of claim 48 further comprising acylating the intermediate of formula (28) under conditions sufficient to yield a compound of formula I.

50. A compound or pharmaceutically acceptable salt thereof in accordance with claim 1, wherein $R_5$, $R_6$, $R_7$, $R_8$, $R_9$ and $R_{10}$ are independently, selected from the group consisting of $(C_1-C_6)$alkyl, $(C_1-C_6)$alkoxy, hydroxy$(C_1-C_6)$alkyl, trihalomethyl, trifluoromethyl, thio$(C_1-C_6)$alkyl, and —$(C_1-C_6)$alkylsulfonyl.

51. A compound or pharmaceutically acceptable salt thereof in accordance with claim 1, wherein $R_{23}$ is selected from the group consisting of $(C_1-C_6)$alkyl.

* * * * *